US006541969B2

(12) United States Patent
Sigal et al.

(10) Patent No.: US 6,541,969 B2
(45) Date of Patent: Apr. 1, 2003

(54) METHOD AND APPARATUS FOR IMPROVING THE VERTICAL RESOLUTION OF NMR LOGS

(75) Inventors: Richard F. Sigal, Spring, TX (US); Ron Cherry, Kingwood, TX (US); Peter Ian Day, Houston, TX (US); James Elmer Galford, Missouri City, TX (US); John C. Bouton, Doylestown, PA (US); Ridvan Akkurt, Kingwood, TX (US); Daniel Lee Miller, Kingwood, TX (US); Manfred G. Prammer, Downingtown, PA (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 09/736,754

(22) Filed: Dec. 14, 2000

(65) Prior Publication Data

US 2001/0033163 A1 Oct. 25, 2001

Related U.S. Application Data

(60) Provisional application No. 60/170,951, filed on Dec. 15, 1999.

(51) Int. Cl.[7] .................................................. G01V 3/00
(52) U.S. Cl. ........................................................ 324/303
(58) Field of Search ................................ 324/300, 301, 324/307, 303, 318, 322

(56) References Cited

U.S. PATENT DOCUMENTS

| | | | |
|---|---|---|---|
| 3,638,484 A | 2/1972 | Tixier ........................... | 73/152 |
| 3,896,668 A | 7/1975 | Anderson et al. ............. | 73/152 |
| 4,686,364 A | 8/1987 | Herron ......................... | 250/256 |
| 4,707,658 A | 11/1987 | Frahm et al. ................ | 324/309 |
| 4,710,713 A | 12/1987 | Taicher et al. ............... | 324/303 |
| 4,717,876 A | 1/1988 | Masi et al. ................... | 324/303 |
| 4,717,877 A | 1/1988 | Taicher et al. ............... | 324/303 |

(List continued on next page.)

FOREIGN PATENT DOCUMENTS

| | | | |
|---|---|---|---|
| EP | 0 295 134 A2 | 12/1988 | ............ G01V/3/32 |
| EP | 0 581 666 A3 | 2/1994 | ............ G01V/3/32 |
| EP | 0 649 035 B1 | 4/1995 | ............ G01V/3/32 |
| GB | 2 056 082 A | 7/1980 | ........... G01N/24/08 |
| WO | WO 98/25164 | 6/1998 | ............ G01V/3/32 |

OTHER PUBLICATIONS

Akkurt et al., "Selection of Optimal Acquisition Parameters for MRIL Logs," SPWLA 37th Annual Logging Symposium, Jun. 16–19, 1996.

Akkurt et al., "NMR Logging of Natural Gas Reservoirs," SPWLA 36th Annual Logging Symposium (Jun. 26–29, 1995).

(List continued on next page.)

Primary Examiner—Edward Lefkowitz
Assistant Examiner—Tiffany A. Fetzner
(74) Attorney, Agent, or Firm—Pennie & Edmonds LLP

(57) ABSTRACT

An method and system are disclosed for NMR echo-train data acquisition and processing for enhanced vertical resolution for a given signal to noise ratio. In one aspect, the method is based on providing an estimate of non-formation signal components and removing the estimate from the NMR signals. Computation of the estimate is done from the data itself or using a direct measurement of non-formation signals. In another aspect, the functions of reducing coherent noise components is separated from the function of reducing the random noise components, to enhance the resolution of the NMR pulse echo data for a given signal to noise ratio (SNR) of the data. Combination processing is disclosed, which enables efficient filtering of the input NMR data for both relatively high and relatively low SNR of the formation data.

15 Claims, 24 Drawing Sheets

U.S. PATENT DOCUMENTS

| | | | |
|---|---|---|---|
| 4,717,878 A | | 1/1988 | Taicher et al. .............. 324/303 |
| 4,728,892 A | | 3/1988 | Vinegar et al. ............. 324/309 |
| 4,933,638 A | | 6/1990 | Kenyon et al. ............. 324/303 |
| 4,939,648 A | | 7/1990 | O'Neill et al. .............. 364/422 |
| 5,023,551 A | | 6/1991 | Kleinberg et al. .......... 324/303 |
| 5,055,787 A | | 10/1991 | Kleinberg et al. .......... 324/303 |
| 5,055,788 A | | 10/1991 | Kleinberg et al. .......... 324/303 |
| 5,086,275 A | | 2/1992 | Roemer ...................... 324/309 |
| 5,212,447 A | | 5/1993 | Paltiel ........................ 324/300 |
| 5,280,243 A | | 1/1994 | Miller ........................ 324/303 |
| 5,291,137 A | | 3/1994 | Freedman ................... 324/303 |
| 5,309,098 A | | 5/1994 | Coates et al. .............. 324/303 |
| 5,350,925 A | | 9/1994 | Watson .................... 250/269.3 |
| 5,363,041 A | | 11/1994 | Sezginer ..................... 324/303 |
| 5,365,171 A | * | 11/1994 | Buess et al. ................ 324/307 |
| 5,381,092 A | | 1/1995 | Freedman ................... 324/303 |
| 5,387,865 A | | 2/1995 | Jerosch-Herold et al. ... 324/303 |
| 5,412,320 A | | 5/1995 | Coates ....................... 324/303 |
| 5,432,446 A | | 7/1995 | Macinnis et al. ........... 324/303 |
| 5,486,762 A | | 1/1996 | Freedman et al. .......... 324/303 |
| 5,497,087 A | | 3/1996 | Vinegar et al. ............. 324/303 |
| 5,498,960 A | | 3/1996 | Vinegar et al. ............. 324/303 |
| 5,517,115 A | | 5/1996 | Prammer .................... 324/303 |
| 5,557,200 A | | 9/1996 | Coates ....................... 324/303 |
| 5,565,775 A | | 10/1996 | Stallmach et al. .......... 324/303 |
| 5,585,720 A | | 12/1996 | Edwards ..................... 324/309 |
| 5,680,043 A | | 10/1997 | Hurlimann et al. ......... 324/303 |
| 5,696,448 A | | 12/1997 | Coates et al. .............. 324/303 |
| 5,705,927 A | | 1/1998 | Sezginer et al. ............ 324/303 |
| 5,796,252 A | | 8/1998 | Kleinberg et al. .......... 324/303 |
| 5,936,405 A | | 8/1999 | Prammer et al. ........... 324/303 |
| 5,977,768 A | | 11/1999 | Sezginer et al. ............ 324/303 |
| 5,992,519 A | | 11/1999 | Ramakrishnan et al. . 166/250.15 |
| 6,005,389 A | * | 12/1999 | Prammer .................... 324/303 |
| 6,049,205 A | * | 4/2000 | Taicher et al. .............. 324/303 |
| 6,111,408 A | | 8/2000 | Blades et al. ............... 324/303 |
| 6,115,671 A | | 9/2000 | Fordham et al. ............... 702/8 |
| 6,121,774 A | * | 9/2000 | Sun et al. ................... 324/303 |
| 6,133,734 A | | 10/2000 | McKeon ..................... 324/303 |
| 6,140,817 A | | 10/2000 | Flaum et al. ............... 324/303 |
| 6,163,153 A | * | 12/2000 | Reiderman et al. ......... 324/314 |
| 6,204,663 B1 | * | 3/2001 | Prammer .................... 324/303 |
| 6,253,155 B1 | | 6/2001 | Hagiwara ...................... 702/9 |
| 6,255,819 B1 | | 7/2001 | Day et al. ................... 324/303 |
| 6,268,726 B1 | * | 7/2001 | Prammer et al. ........... 324/303 |
| 6,326,784 B1 | * | 12/2001 | Ganesan et al. ............ 324/303 |
| 6,388,441 B1 | * | 5/2002 | Chen .......................... 324/303 |

OTHER PUBLICATIONS

Brown et al., "Nuclear Magnetism Logging," Transactions of the American Institute of Mining, Metallurgical, and Petroleum Engineers, vol. 219 (1960), pp. 199–207.

Cannon et al., "Quantitative NMR Interpretation," Society of Petroleum Engineers, SPE 49010, 1998.

Chandler et al., "Improved Log Quality with a Dual–Frequency Pulsed NMR Tool," *Society of Petrtoleum Engineers* (1994) pp. 23–35.

Chandler et al., "Reliable Nuclear Magnetism Logging—With Examples in Effective Porosity and Residual Oil Saturation," SPWLA—28th Annual Logging Symposium, vol. 1, Manuscript C, (1987).

Chen et al., "Improving the Accuracy of NMR Relaxation Distribution Analysis in Clay–Rich Reservoirs and Core Samples," paper SCA 9702, in 1997 international symposium proceedings: Society of Professional Well Log Analysts, Society of Core Analysts Chapter–at–large, p. 10, 1997.

Clavier et al., "Theoretical and Experimental Bases for the Dual–Water Model for Interpretation of Shaly Sands," Society of Petroleum Engineers Journal, 1984, pp. 153–168.

Coates et al., "An Investigation of a New Magnetic Resonance Imaging Log," National SPWLA Convention (Jun. 18, 1991), pp. 1–24.

Coates et al., "Applying NMR Total and Effective Porosity to Formation Evaluation," Society of Petroleum Engineers, Inc., SPE 38736, 1997.

Coates et al., "Core Data and the MRIL Show—A New Approach to 'Formation Factor,'" National SPWLA Convention (Jun. 15, 1992), pp. 1–15.

Coates et al., "A New Approach to Improved Log–Derived Permeability," SPWLA Fourteenth Annual Logging Symposium, May 6–9, 1973, pp. 1–27.

Coates et al., "The Magnetic Resonance Imaging Log Characterized by Comparison With Petrophysical Properties and Laboratory Core Data," Society of Petroleum Engineers, SPE 22723, 1991, pp. 627–635.

Dunn et al., "A Method for Inverting NMR Data Sets With Different Signal to Noise Ratios," SPWLA 39th Annual Logging Symposium, May 26–29, 1998.

Edwards et al., "Improved NMR Well Logs From Time–Dependent Echo Filtering," SPWLA 37th Annual Logging Symposium, Jun. 16–19, 1996.

Edwards et al., "Effects of Tool Design and Logging Speed on $T_2$ NMR Log Data," SPWLA 38th Annual Logging Symposium, Jun. 15–18, 1997.

Freedman et al., "Combining NMR and Density Logs for Petrophysical Analysis in Gas–Bearing Formations," SPWLA 39th Annual Logging Symposium, May 26–29, 1998.

Gallegos et al., "A NMR Technique for the Analysis of Pore Structure: Application to Materials with Well–Defined Pore Structure," Journal of Colloid and Interface Science, vol. 119, No. 1, Sep. 1987, pp. 127–140.

Güven, "Molecular Aspects of Clay–Water Interactions," CMS Workshop Lectures, vol. 4.

Herrick et al., "An Improved Nuclear Magnetism Logging System and its Application to Formation Evaluation," Society of Petroleum Engineers, SPE 8361, 1979.

Hou et al., "Nuclear Magnetic Resonance Logging Methods for Fluid Typing," Society of Petroleum Engineers, Inc., SPE 48896, 1998.

Jackson et al., "Western Gas Sands Project Los Alamos NMR Well Logging Tool Development," Los Alamos National Laboratory (Oct. 1981—Sep. 1982) pp. 1–28.

Jackson, Japsper A., "Nuclear Magnetic Resonance Well Logging," The Log Analyst, Sep.–Oct., 1984, pp. 16–30.

Kenyon et al., "Pore–Size Distribution and NMR in Microporous Cherty Sandstones," SPWLA Thirtieth Annual Logging Symposium (Jun. 11–14, 1989), pp. 1–24.

Kleinberg et al., "Novel NMR Apparatus for Investigating an External Sample," *Journal of Magnetic Resonance*, (1992) pp. 466–485.

Kleinberg et al., "Nuclear Magnetic Resonance of Rocks: $T_1$ vs. $T_2$," Society of Petroleum Engineers, SPE 26470, 1993, pp. 553–563.

Kleinberg et al., "NMR Properties of Reservoir Fluids," The Log Analyst, Nov.–Dec. 1996, pp. 20–32.

Menger et al., "A New Algorithm for Analysis of NMR Logging Data," Society of Petroleum Engineers, Inc., SPE 49013, 1998.

Miller et al., "Spin Echo Magnetic Resonance Logging: Porosity and Free Fluid Index Determination," *Society of Petroleum Engineers*, SPE 20561 (1990), pp. 321–334.

Morriss et al., "Field Test of an Experimental Pulsed Nuclear Magnetism Tool," SPWLA Annual Logging Symposium (Jun. 13–16, 1993), pp. 1–23.

Morriss et al., "Hydrocarbon Saturation and Viscosity Estimation from NMR Logging in the Belridge Diatomite," 35th SPWLA Annual Logging Symposium (Jun. 19–22, 1994), pp. 1–24.

Prammer et al., "Theory and Operation of a New, Multi-Volume, NMR Logging System," SPWLA 40th Annual Logging Symposium, May 30–Jun. 3, 1999.

Prammer et al., "A New Multiband Generation of NMR Logging Tools," Society of Petroleum Engineers, SPE 49011, 1998.

Prammer et al., "Measurements of Clay–Bound Water and Total Porosity by Magnetic Resonance Logging," Society of Petroleum Engineers, SPE 36522, 1996.

Prammer, M.G., "NMR Pore Size Distributions and Permeability at the Well Site," *Society of Petroleum Engineers*, SPE 28368, (1994) pp. 55–64.

Regrim, "Capter 8: Clay–Water System" in *Clay Mineralogy*, $2^{nd}$ Ed. 1968.

*Schlumberger Technology News—Oilfield Bulletin*, "Fifth Generation Nuclear Magnetic Resonance Logging Tool: A Major Advance in Producibility Measurement Technology," (Jul. 1995) (2 pp.).

*Schlumberger Wireline & Testing*, "Combinable Magnetic Resonance tool reliably indicates water–free production and reveals hard–to–find pay zones," (Jun. 1995).

Singer et al., "Fast NMR Logging for Bound Fluid and Permeability," SPWLA 38th Annual Logging Symposium, Jun. 15–18, 1997.

* cited by examiner

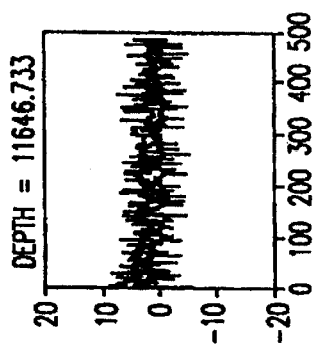
Fig. 4D
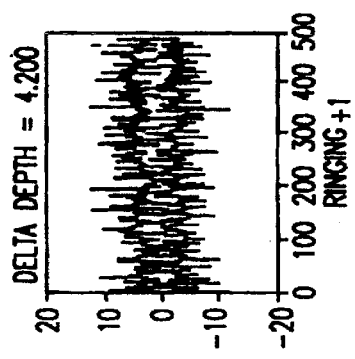
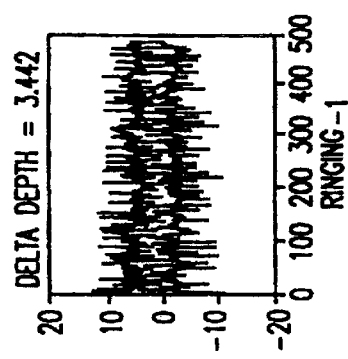
Fig. 4E
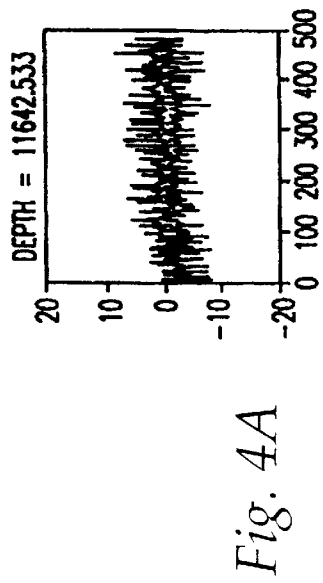
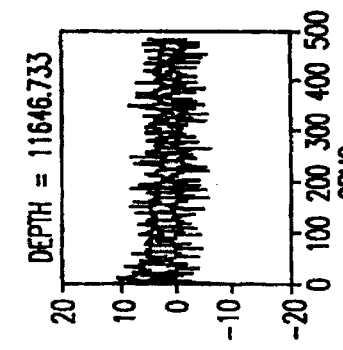
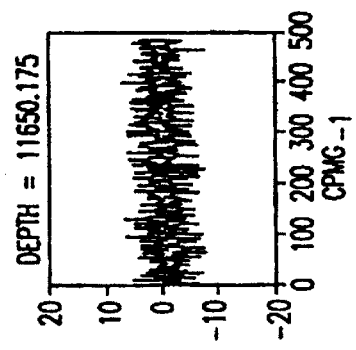
Fig. 4A
Fig. 4B
Fig. 4C SEQUENTIAL PAP's OVERLAPPING PAP's

METHOD AND APPARATUS FOR IMPROVING THE VERTICAL RESOLUTION OF NMR LOGS

This application claims the benefit of Provisional application Ser. No. 60/170,951, filed Dec. 15, 1999.

FIELD OF THE INVENTION

The present invention concerns nuclear magnetic resonance (NMR) logging and more specifically relates to a method and apparatus for NMR data acquisition and processing, which for a given signal-to-noise ratio (SNR) improve the vertical resolution of data logs acquired using NMR logging tools.

BACKGROUND OF THE INVENTION

In oil and gas exploration it is desirable to understand the structure and properties of the geological formation surrounding a borehole, in order to determine if the formation contains hydrocarbon resources (oil and/or gas), to estimate the amount and producibility of hydrocarbon contained in the formation, and to evaluate the best options for completing the well in production. A significant aid in this evaluation is the use of wireline logging and/or logging-while-drilling (LWD) measurements of the formation surrounding the borehole (referred to collectively as "logs" or "log measurements"). Typically, one or more logging tools are lowered into the borehole and the tool readings or measurement logs are recorded as the tools traverse the borehole. These measurement logs are used to infer the desired formation properties.

In recent years nuclear magnetic resonance (NMR) logging has become very important for purposes of formation evaluation and is one of the preferred methods for determining formation parameters. Improvements in the NMR logging tools, as well as advances in data analysis and interpretation allow log analysts to generate detailed reservoir description reports, including clay-bound and capillary-bound related porosity, estimates of the amounts of bound and free fluids, fluid types (i.e., oil, gas and water), permeability and other properties of interest.

NMR tools used in practical applications include, for example, the centralized MRIL® tool made by NUMAR Corporation, a Halliburton company, and the sidewall CMR tool made by Schlumberger. The MRIL® tool is described, for example, in U.S. Pat. No. 4,710,713 to Taicher et al. and in various other publications including: "Spin Echo Magnetic Resonance Logging: Porosity and Free Fluid Index Determination," by Miller, Paltiel, Gillen, Granot and Bouton, SPE 20561, 65th Annual Technical Conference of the SPE, New Orleans, La., Sep. 23–26, 1990; "Improved Log Quality With a Dual-Frequency Pulsed NMR Tool," by Chandler, Drack, Miller and Prammer, SPE 28365, 69th Annual Technical Conference of the SPE, New Orleans, La., Sep. 25–28, 1994. Certain details of the structure and the use of the MRIL® tool, as well as the interpretation of various measurement parameters are also discussed in U.S. Pat. Nos. 4,717,876; 4,717,877; 4,717,878; 5,212,447; 5,280,243; 5,309,098; 5,412,320; 5,517,115, 5,557,200; 5,696,448 and 5,936,405. The structure and operation of the Schlumberger CMR tool is described, for example, in U.S. Pat. Nos. 4,939,648; 5,055,787 and 5,055,788 and further in "Novel NMR Apparatus for Investigating an External Sample," by Kleinberg, Sezginer and Griffin, J. Magn. Reson. 97, 466–485, 1992; and "An Improved NMR Tool Design for Faster Logging," D. McKeon et al., SPWLA 40$^{th}$ Annual Logging Symposium, May–June 1999. The content of the above patents is hereby expressly incorporated by reference for all purposes, and all non-patent references are incorporated by reference for background.

NMR tools of the type discussed above generally measure the time for hydrogen nuclei present in the earth formation to realign their spin axes, and consequently their bulk magnetization, either with an externally applied magnetic field, or perpendicularly to the magnetic field, after momentary reorientation due to the application of specific radio frequency (RF) pulses. The externally applied magnetic field is typically provided by a magnet disposed in the tool. The spin axes of the hydrogen nuclei in the earth formation are, in the aggregate, caused to be aligned with the magnetic field induced in the earth formation by the magnet. The NMR tool includes an antenna positioned near the magnet and shaped so that a pulse of radio frequency (RF) power conducted through the antenna induces a magnetic field in the earth formation orthogonal to the field induced by the magnet. The RF pulse has a duration predetermined so that the spin axes of the hydrogen nuclei generally align themselves perpendicular both to the orthogonal magnetic field induced by the RF pulse and to the externally applied magnetic field. After the pulse ends, the nuclear magnetic moment of the hydrogen nuclei gradually relax, i.e., return to their alignment with the externally applied magnetic field; at the same time an antenna, which is typically the same as the one used by the initial pulse, is electrically connected to a receiver, which detects and measures voltages induced in the antenna by precessional rotation of the spin axes of the hydrogen nuclei.

An actual NMR measurement involves a plurality of pulses grouped into pulse sequences, most frequently of the type known in the art as Carr-Purcell-Meiboom-Gill (CMPG) pulsed spin echo sequences. As known in the art, each CPMG sequence consists of a 90-degree (i.e., $\pi/2$) pulse followed by a large number of 180-degree (i.e., $\pi$) pulses. The 90-degree pulse rotates the proton spins into the transverse plane and the 180-degree pulses generate a sequence of spin echoes by refocusing the transverse magnetization after each spin echo.

It should be apparent that it is important for the NMR measurements to register only signals that are generated by the formation of interest. However, non-formation signals—often referred to as "offset" or "ringing" signals—arise for a variety of reasons. For example, they may be caused by the high-sensitivity tool electronics (e.g., "offsets"), or may be due to magnetostrictive effects (e.g., "ringing") that arise from interactions between pulsed magnetic fields and electronic or magnetic components in the tool. For example, when RF pulses are applied to the antenna, the magnet can become physically deformed by magnetostriction. After each RF pulse is turned off, the magnet tends to return to its original shape in a series of damped mechanical oscillations, known as "ringing." Ringing induces voltages in the antenna, which can interfere with measurement of the voltages induced by the spin echoes.

A method known in the art for reducing the effect of offsets, ringing and possibly other non-formation signals is to make spin echo measurements in predetermined cycles. Typically, two pulse sequences of opposite phase are acquired to cancel electronic offsets and 180-degree ringing. The pair of pulse sequences is called a phase-alternated pair (PAP). PAP measurements are performed by making a second set of spin echo measurements starting with an original transverse alignment (90 degree) RF pulse, which is inverted in phase from the 90 degree pulse used to start the first set of spin echo measurements. Voltages induced in the antenna during the second set of spin echo measurements are inverted in polarity from the voltages induced in the first set of measurements. The signals from the second set of measurements can then be subtracted from the signals in the first set of measurements to substantially remove coherent noise, such as the ringing-induced signals. (For simplicity, in the following discussion "ringing" will be used as a catch-all term designating undesirable non-formation signals). Accordingly, in the "PAP method" successive echo-train signals are acquired from the formation that are alternately in-phase and anti-phase with respect to signals that are generated outside the formation; thus, a typical PAP simply comprises any adjacent pair of in-phase and anti-phase CPMG echo-trains. An implicit assumption in this operation is that the tool-related, non-formation signals in an echo-train can somehow be characterized, and that they change little, or even not at all, between successive echo-trains.

Mathematically, the PAP method can be illustrated as follows. Suppose that an individual spin echo train ($CPMG_0$) can be characterized as a summation of a decaying NMR signal from the formation ($S_0$), a non-formation signal ($O_0$), and random or thermal noise ($n_0$), so that $CPMG_0 = S_0 + O_0 + n_0$. The subsequent phase-alternated echo-train ($CPMG_1$), is then given by $CPMG_1 = -S_1 + O_1 + n_1$. Since changes in the non-formation signal are assumed to be minimal, the difference between the two echo-trains (PAP) cancels the non-formation signals, leaving an echo-train that is a composite of the signals and the noise, i.e.:

$$PAP = (S_0 + S_1) + n_\Delta.$$

Accordingly, in the prior art non-formation noise is removed using the above PAP process, in which one or more phase alternate pair signals are subtracted to remove the ringing. The two acquisition sequences in each phase alternate pairs must be separated in time by $T_W$, the time to repolarize the media. During logging, the tool is moving at a speed v, so that the PAPs are separated by a distance equal to $v*T_W$. Clearly, this limits the vertical resolution achievable with the tool.

It is thus apparent that to minimize or ideally eliminate non-formation components of the input signal, in accordance with the prior art it is the PAP, rather than the individual echo-train that becomes the basic measured element, which is then processed in similar manner to NMR echo-trains acquired in a laboratory. A potential advantage of the prior art method is that it results in increased SNR of the output signal due to the averaging operation. As discussed above, however, using PAPs as opposed to single echo trains as basic measurement units also introduces a delay that places various constraints on both the achievable logging speed and the vertical resolution of NMR logs.

As noted, prior art methods use a single operation to accomplish both the ringing elimination, as well as the signal-to-noise improvement by means of experiment stacking. One requirement of the prior art methods is to select an amount of stacking necessary for a desired SNR that includes, with equal weight, every PAP at every acquired frequency. This is typically referred to as "boxcar" filtering of the data. For an NMR tool operating at a single frequency, the number of PAPs stacked is simply one or more. For NMR logging tools, such as the MRIL Prime, operating at N frequencies, the numbers of PAPs stacked must be a multiple of N. Since each PAP comprises two echo-trains, the minimum stacking for the MRIL tool is two times the number of acquired frequencies. There are two problems associated with this approach. First, in formations with high signal-levels, the approach results in more stacking than is necessary to provide adequate signal-to-noise ratio. On the other hand, for those formations with lower signal-levels, in which more stacking is required to obtain adequate SNR, it is necessary to select an amount of stacking, which is a multiple of the minimum stacking. This is undesirable at least because the extra averaging introduces undesirable processing delays and, as shown below, reduces the maximum vertical resolution.

As shown in the detailed disclosure, in accordance with the present invention an alternative approach can be used where the ringing and random noise components are processed in two steps with possibly different filters. The results show that the (vertical) resolution of NMR logs can be improved in many cases. The output of the proposed processing method is consistently less noisy and more robust even in those cases where there is not a significant vertical resolution improvement compared to the conventional boxcar filter approach.

Focusing next on another deficiency associated with the prior art, as a consequence of the PAP method, the "best-possible" effective vertical resolution of an NMR log acquired with a moving tool is a combination of both the inherent vertical resolution of the tool antenna—the antenna aperture—and the distance traveled between the pair of echo-train measurements that comprise a PAP. As discussed above, however, in many logging situations the vertical resolution is further compromised by the need to average data from multiple PAPs to ensure an adequate signal-to-noise ratio (SNR) for confident data analysis. For example, it is known in the art to improve the SNR of NMR well logging measurements by averaging a plurality of PAPs, typically eight or more.

Depending on the specific "PAP accounting method" employed, echo-trains can form PAPs in a number of different ways. For example, in one method, two adjacent echo-trains form a single PAP, three adjacent echo-trains form two PAPs, and four echo-trains form three PAPs. In an alternative method, while two adjacent echo-trains still form a single PAP, four adjacent echo-trains might be needed to form two PAPs, with six adjacent echo-trains needed to form three. See FIG. 11A. Illustrated in the figure is the "overlapping" mode of operation (of the CMR tool discussed above), where one PAP is acquired every sample interval. As illustrated, in an overlapping mode the two CPMGs overlap half of the sample interval, and the tool relies on the wait time to polarize the hydrogen spins for the NMR measurement. The logging speed (v) of the tool depends on a number of factors, primarily the sample interval and the measurement wait time.

As shown in FIG. 11B in a different embodiment of the CMR tool (CMR Plus), to speed up the measurements the tool uses a new measurement sequence called a sequential PAP. As illustrated, the tool acquires a single CPMG per sample interval, and the phase of each successive CPMG is shifted 180 degrees. A PAP is formed every sample interval by combining the most recent CPMG with the prior CPMG. This measurement sequence allows the tool to move faster, however, it is apparent that the number of independent CPMGs is reduced, which increases the noise level.

In earlier models of the MRIL tool, the typical logging speed used to acquire NMR data is sufficiently low, so that the effective vertical resolution of the NMR log is dominated by the need to stack multiple PAPs to obtain adequate SNR. For the multi-frequency MRIL Prime tool, however, the use of multiple NMR measurement frequencies is conceptually equivalent to the simultaneous acquisition of multiple passes with the earlier logging tools. Thus, MRIL Prime logs could be acquired at faster logging speeds, with the required SNR obtained by stacking multiple PAPs across the frequency bands.

Unfortunately, in high-signal formations (e.g., high porosity, oil-or water-filled rocks), where the logging speeds can be comparatively fast, the effective vertical resolution of the NMR log becomes dominated by the tool movement during a single PAP. For example, with a recovery time of 10 seconds between echo-trains in a PAP, with PAPs acquired at all possible frequencies, the elapsed time between the first echo-train in the first-frequency PAP and the second echo-train for the last-frequency PAP, is close to 20 seconds. At a logging speed of 900 ft/hr (15 ft/min), the MRIL tool will move approximately 5 feet during this measurement: when combined with the inherent vertical resolution of the antenna (which is approximately 2 feet), the effective vertical resolution becomes roughly 7 feet.

Enhancing the resolution of the logs is a significant problem, because subsurface formations are generally heterogeneous, so that porosity, saturation and lithology vary with position. A common example of heterogeneity is the presence in the formation of geological layers, or beds. Because logging tools have a nonzero volume of investigation, more than one layer may lie within the volume of investigation of a tool. In such cases, the petrophysical evaluation of one layer may be distorted by the presence of another layer falling within the larger volume of investigation of the tool. The above phenomenon leads to a specific problem in the analysis of subsurface formations that include one or more underground layers, especially when the layers are thin compared with the vertical resolution of the measuring tool. Such layers have become subject to significant commercial interest because of their production potential. Any knowledge about the composition and properties of such layered formations that helps better estimate their production potential has thus become increasingly valuable.

Clearly, to make the best use of the NMR logging tools, it is necessary that the current reliance on the PAP as the basic measured element be reduced. Clearly, if for example the MRIL Prime data can be acquired and/or processed in such a manner that a single echo-train, rather than a PAP, becomes the basic unit of measurement, then it becomes possible to provide an NMR log with an effective vertical resolution much closer to the inherent resolution defined by the length of the tool antenna. Using the assumptions in the example above, if it was only necessary to stack echo-trains from four frequencies to obtain adequate SNR, the elapsed time of the measurements would be about 5 seconds, during which time the MRIL tool would move approximately 1 foot, resulting in the effective vertical resolution of the NMR log of approximately 3 feet. It is clear therefore that any mechanism that for a given SNR supported by the formation can increase the vertical resolution of the tool without decreasing the logging speed is highly desirable.

SUMMARY OF THE INVENTION

Accordingly, it is an object of the present invention to overcome deficiencies associated with the prior art and in particular to provide a method and system for improving the resolution of borehole NMR logging measurements and for suppressing artifacts in NMR data obtained from logging measurements.

These and other objects are accomplished in accordance with a preferred embodiment of the present invention by a novel approach in which non-formation, i.e., ringing, signals are characterized and removed from the underlying NMR spin echo signals in separate steps. In particular, to analyze the ringing signals it is first proposed to combine two or more acquisition sequences in such a matter as to obtain an estimate of the ringing component of the signal, which is assumed to be a constant or a slowly varying function. In the following step of the process, various signal processing or statistical methods are applied to remove the estimated ringing component from the acquisition sequences. In a second embodiment, the ringing component of the signal is estimated by direct measurement using a separate NMR pulse sequence, which in a specific implementation is a standard CMPG pulse echo sequence without the leading 90 degree pulse. Such sequence will generally contain ringing but not any decay signals, i.e., formation signals. Once the ringing constant (or slowly varying function) is established, it is removed from the NMR acquisition data. In both embodiments, experiment stacking is performed as known in the art to increase the signal to noise ratio of the signal. In a preferred embodiment, the steps of ringing estimation and removal and the step of experiment stacking can be performed as a single pass through the acquired data, CPMG by CPMG, typically in a successive or chronological fashion. Alternatively, the method can have the first two steps performed in a single pass through the acquired data in a successive fashion, with the third step performed as a second pass. Following these steps, the NMR signal is processed as known in the art to obtain parameters of interest characterizing the formation.

In particular, according to this invention a system and method are proposed for the interpretation of NMR echo-train data. In one aspect, the invention is a method for determining properties of geologic formations using nuclear magnetic resonance (NMR) logging, comprising: providing a plurality of phase alternated NMR pulse echo trains from a geologic formation; estimating non-formation signal contribution in the plurality of NMR pulse echo trains; removing the estimated non-formation signal contribution from at least some of the plurality of NMR pulse echo trains; and determining properties of the geologic formation based at least in part on NMR pulse echo trains in which the estimated non-formation signal contribution had been removed. In a preferred embodiment, the NMR pulse echo trains are Carr-Purcell-Meiboom-Gill (CMPG) spin echo trains. Further, non-formation signal contribution is estimated from two or more of the plurality of CPMG spin echo trains, preferably using one or more phase-alternated pair(s) (PAPs) of CPMG spin echo trains. In a specific implementation two PAPs are used that are formed by a current CPMG spin echo train ($CPMG_0$) and an immediately preceding ($CPMG_{-1}$) and an immediately following ($CPMG_{+1}$) phase alternated CPMG spin echo trains.

In another embodiment, non-formation signal contribution is estimated using a separate NMR pulse echo train, which preferably is a CPMG spin echo train without an initial $\pi/2$ pulse.

In another aspect, the invention is a method for increasing the resolution of NMR log data obtained using a multi-frequency NMR tool having N operating frequencies, comprising: (a) providing a NMR pulse echo signal comprising components corresponding to at least two of the N operating frequencies of the tool; (b) separating the provided pulse echo signal into two or more data-flow paths, each data flow path corresponding to an operating frequency of the tool; (c) filtering the signal in each separate data flow path using a first filter designed to reduce the contribution of non-formation signal components; and (d) filtering the output signal from the first filter to achieve a predetermined signal-to-noise ratio (SNR) for a given resolution of the NMR log data. In a preferred embodiment, step (d) is performed using a tapered filter, which may be a Hamming filter. In a preferred embodiment, the first filtering operation in step (c) is performed on phase alternated pairs (PAPs) of signals.

In yet another aspect, the invention is a system for increasing the resolution of NMR log data obtained using a multi-frequency NMR tool having N operating frequencies, comprising: means for providing a NMR pulse echo signal comprising components corresponding to at least two of the N operating frequencies of the tool; means for separating the provided pulse echo signal into two or more data-flow paths, each data flow path corresponding to an operating frequency of the tool; means for filtering the signal in each separate data flow path using a first filter designed to reduce the contribution of non-formation signal components; and means for filtering the output signal from the first filter to achieve a predetermined signal-to-noise ratio (SNR) for a given resolution of the NMR log data.

BRIEF DESCRIPTION OF THE DRAWINGS

FIGS. 4A, 4B, 4C, 4D, 4E, and 4F (referred to herein collectively as FIG. 4) illustrate intermediate results for the Ringing Estimation step and results after Ringing Elimination step (step 2) used in a preferred embodiment of this invention;

DETAILED DESCRIPTION OF THE PREFERRED EMBODIMENTS

I. The System

Figure 1:
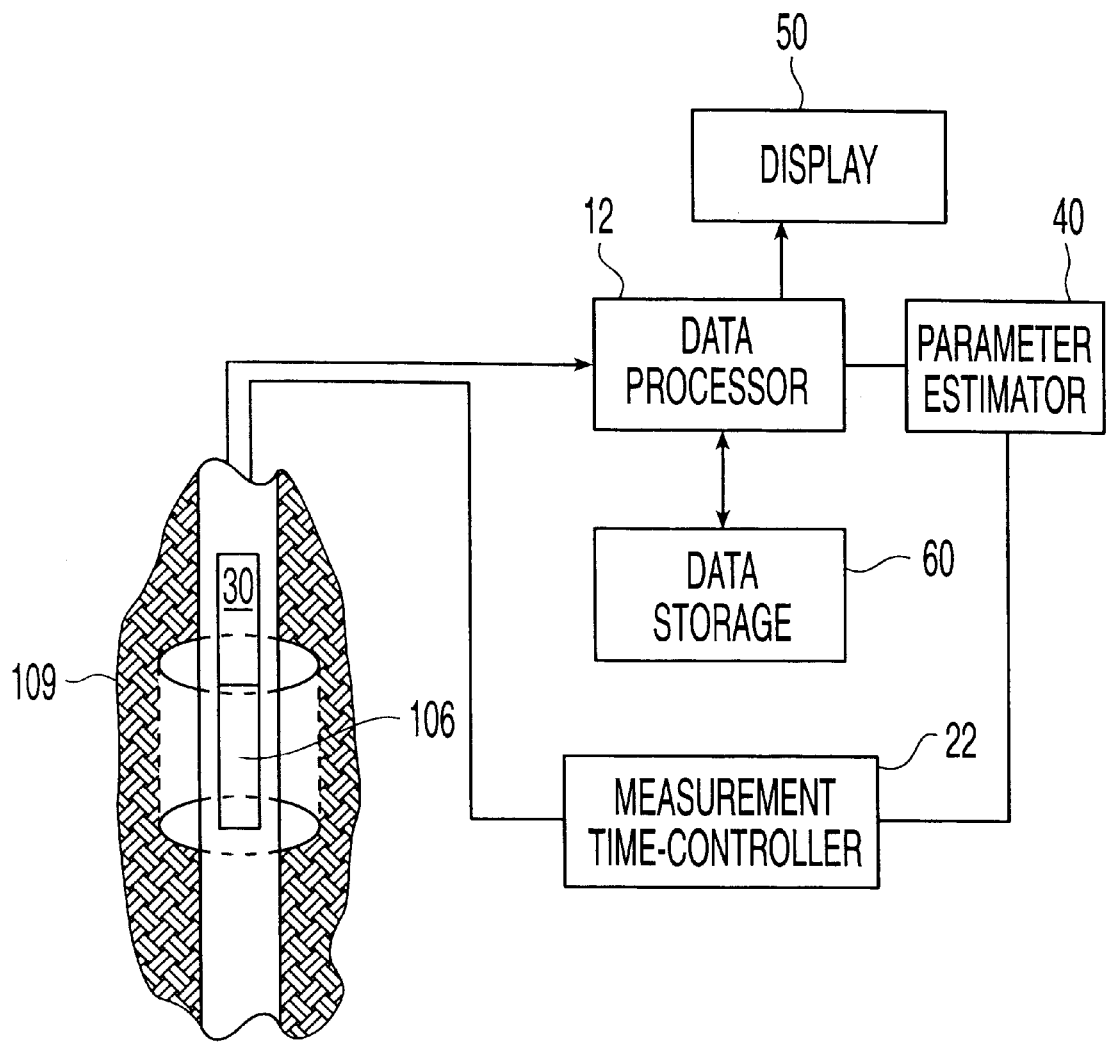
FIG. 1 is a block diagram of a NMR logging system used in accordance with the present invention.

FIG. 1 is a block diagram of a system in accordance with a specific embodiment of the present invention, which shows individual block components for controlling data collection, processing of the collected data and displaying the measurement results. In FIG. 1 a logging tool 106 comprises an NMR probe controller 30 and pulse echo detection electronics and is lowered in a borehole drilled in the formation 109. The output signal from the tool detection electronics is processed by data processor 12 to record NMR pulse echo data from the tool and analyze the relaxation characteristics of the materials surrounding the borehole. The output of the data processor 12 is fed to parameter estimator 40. Measurement cycle controller 22 provides an appropriate control signals to the probe. The processed data from the log measurements is stored in data storage 60. Data processor 12 is connected to display 50, which is capable of providing a graphical display of one or more measurement parameters, preferably superimposed on display data from data storage 60. The components of the system of the present invention shown in FIG. 1 can be implemented in hardware or software, or any combination thereof suitable for practical purposes.

Figure 2:
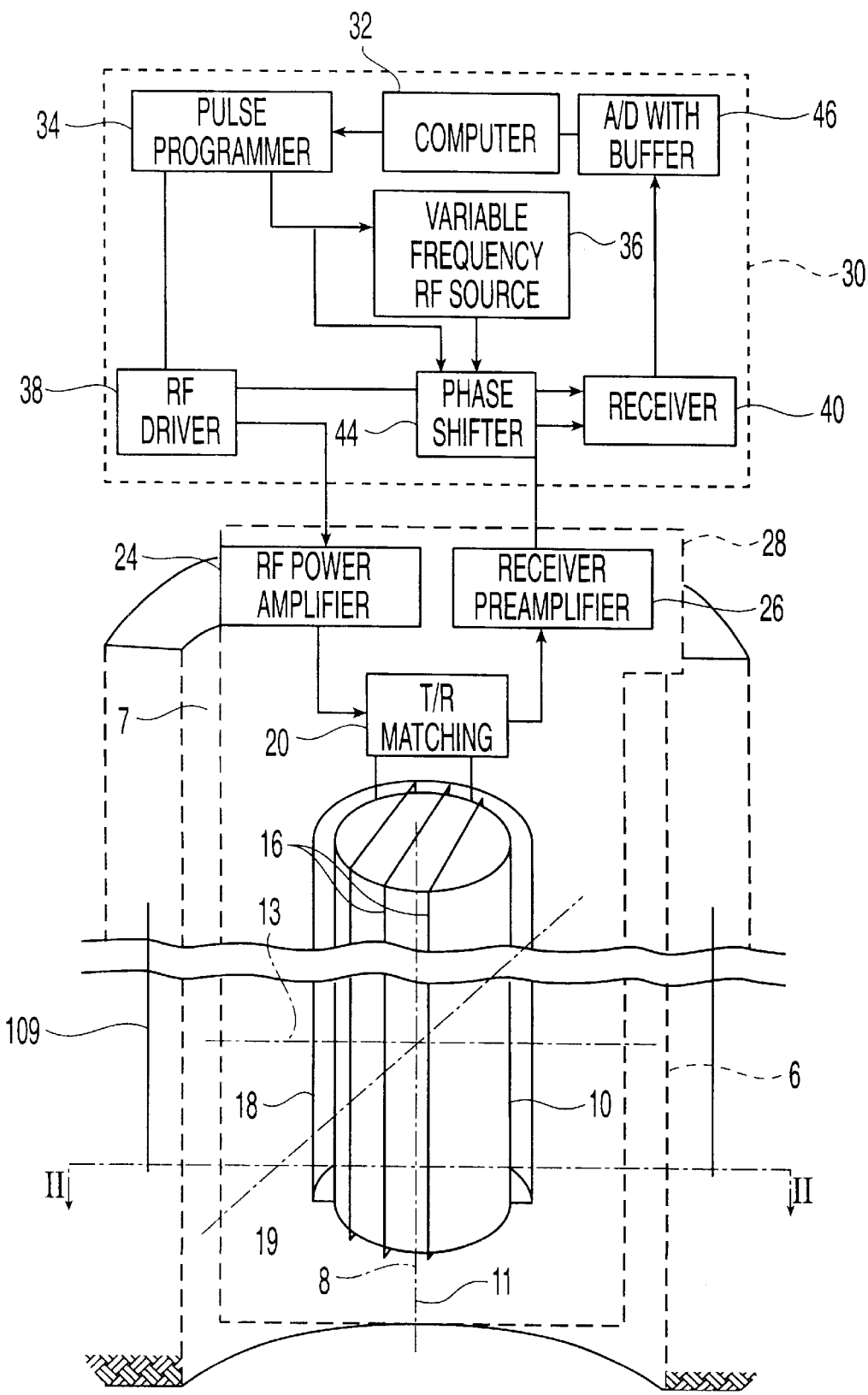
FIG. 2 is a partially schematic, partially block diagram of a NMR logging tool and attached electronics used in a preferred embodiment.

Reference is now made to FIG. 2, which illustrates in a semi-block diagram form an NMR logging apparatus, such as the MRIL Prime tool of Numar Corporation (a Halliburton Company), which can be used for NMR measurements in accordance with the present invention. In standard operation, first portion 6 of the tool is arranged to be lowered into a borehole 7 having a borehole longitudinal axis 8 in order to examine properties of the geologic formation in the vicinity of borehole 7.

The first portion comprises a generally cylindrical permanent magnet 10, preferably having a longitudinal axis 11, which is preferably coaxial with the longitudinal axis 8 of the borehole. Alternatively, a plurality of permanent magnets 10 may be employed. Permanent magnet 10 preferably has uniform magnetization substantially perpendicular to the longitudinal axis of the logging tool, which is parallel to the longitudinal axis 8 of the borehole 7.

The first portion 6 also comprises one or more coil windings 16, which preferably are arranged on top of the permanent magnet and form the tool antenna. The magnetization direction 13 created by the antenna is substantially perpendicular to the longitudinal axis 8 of the bore hole. The coil windings 16, together with a transmitter/receiver (T/R) matching circuit 20 define a transmitter/receiver (T/R) circuit. T/R matching circuit 20 typically includes a resonance capacitor, a T/R switch and both to-transmitter and to-receiver matching circuitry and is coupled to a first RF power amplifier 24 and to a receiver pre-amplifier 26.

The permanent magnet 10 and coil windings 16 are preferably housed in a non-conductive, non-ferromagnetic protective housing 18. The housing and its contents will hereinafter be referred to as the probe 19.

In operation, the probe along with RF amplifier 24, preamplifier 26 and T/R matching circuit 20, designated collectively as housing 28 are passed through the borehole. Alternatively, some of the above elements may be located above ground in housing 30.

Disposed in a housing indicated in FIG. 2 by block 30, is a control circuitry, including a computer 32, which provides a control output to a pulse programmer 34. Pulse programmer 34 controls the operation of phase shifter 44, as well as an RF driver 38, which drives RF power amplifier 24. Pulse programmer 34 controls the operation of a variable frequency RF source 36, the output of which is passed through phase shifter 44 to the RF driver 38. The signal from RF driver 38 is amplified in RF power amplifier 24 and passed through T/R matching circuit 20 to the receiving coil antenna 16.

NMR signals from excited nuclei in the formation surrounding the borehole are picked up by the receiving antenna 16 and passed through T/R matching circuit 20 to RF receiver pre-amplifier 26, the output of which is supplied to an RF receiver 40 which also receives an input from phase shifter 44. Receiver 40 outputs via an A/D converter with a buffer 46 to the computer 32 for providing desired well logging output data for further use and analysis.

Further details of the construction and operation of the tool used in accordance with a preferred embodiment of the present invention can be found in U.S. Pat. Nos. 4,710,713 4,717,876; 4,717,877; 4,717,878; 5,212,447; 5,280,243; 5,309,098; 5,412,320; 5,517,115, 5,557,200 and 5,696,448. The content of the above patents is hereby expressly incorporated by reference. It will be appreciated that while the MRIL tool is used in a preferred embodiment, any other tool notably the CMR and CMR-Plus tools by Schlumberger, or other available tools, such as those by Baker-Atlas and Computalog, as well as logging-while-drilling (LWD) tools, appropriately programmed, can also be used in alternative embodiments.

II. The Methods

In accordance with one aspect of the present invention, a novel approach is proposed for reducing the level of non-formation signals, i.e., ringing, in which ringing signals are characterized and removed from the underlying NMR pulse echo signals in separate steps. Once the estimated ringing component is removed from the acquisition sequence(s), in accordance with one embodiment of the invention, standard NMR processing methods are applied to derive petrophysical properties of the formation being investigated. In accordance with another aspect of the invention, which is described in Section D below, additional pre-processing is applied to the signal to further improve the resolution of the tool.

First is considered a method for reducing the level of ringing in the signal for a given signal-to-noise ration (SNR) using a multi-step approach. In a preferred embodiment, there are three conceptual steps, broadly designated: Ringing Estimation; Ringing Elimination; and Experiment Stacking.

A. Ringing Estimation

In a preferred embodiment of the invention, an estimated ringing level for each measurement is obtained in the Ringing Estimation step through use of a three-operation process. The three operations include: (a) providing a Basic Ringing Estimate; (b) providing an Echo Time Average; and (c) computing a PAP Mean Ringing Average.

A.1. Basic Ringing Estimate

In accordance with the present invention, two methods are proposed for determining the Basic Ringing Estimate. In a first, preferred method, computing the Basic Ringing Estimate is a data-driven determination from the echo-trains that comprise the phase-alternated pairs (PAPs). In accordance with an alternative embodiment, the Basic Ringing Estimate is computed using a direct measurement (DM) of the ringing from a special "ringing echo-train" acquired immediately before or after a normal echo-train.

A1.a. Basic Ringing Estimate [PAP]

The Basic Ringing Estimate [PAP] operation in accordance with the preferred embodiment comprises summing the current measurement CPMG spin echo train with one of more of the current measurement's PAP CPMG echo trains. This operation is performed on an echo by echo basis for each Phase Alternate Pair separately, which results in one or more basic ringing estimate vectors, the length of which is determined by the length of the echo trains.

In particular, in a preferred embodiment the method uses the current measurement CPMG (denoted $CPMG_0$—which is a vector having N elements, where N is the length of the spin-echo sequence) with the two nearest CPMG echo trains, with which it forms PAPs, i.e., the "preceding" alternate phase echo train ($CPMG_{-1}$) and the "following" alternate phase echo train ($CPMG_{+1}$)—to create two estimates of the basic ringing estimate vectors, each having N elements. Mathematically, the basic ringing estimates can be expressed as follows:

$$Ringing_{-1}(n) = \frac{CPMG_0(n) + CPMG_{-1}(n)}{2} \quad \text{Eqn. (1)}$$

$$Ringing_{+1}(n) = \frac{CPMG_0(n) + CPMG_{+1}(n)}{2}$$

Because the CPMG echo trains are acquired in quadrature, it will be appreciated that the operations described above, and in subsequent equations, are performed in the complex domain, i.e., by treating separately the real and imaginary signal input channels.

Assuming that the CPMG echo-trains acquired at a single frequency can be represented by the following sequence relative to some arbitrary starting sample at 0:

. . .
$-S_{-3}+O$
$S_{-2}+O$
$-S_{-1}+O$
$S_0+O$
$-S_{+1}+O$
$S_{+2}+O$
$-S_{+3}+O$
. . .

where $S_0$ is the formation signal at depth 0, O is the tool-generated non-formation signal, and the signs are arranged such that each adjacent pair is a PAP. In the notation used above, $CPMG_0$ is equal to $S_0+O$, and necessarily contains random or thermal noise that arises in both the formation and non-formation signals. The random noise component is omitted for convenience.

Using Eqn. (1), the 2 PAPs incorporating ($S_0+O$) are summed in such a manner that they yield (in vector notations):

$$\left(\frac{(\bar{S}_0 - \bar{S}_{-1}) + 2\bar{O}}{2} + \frac{(\bar{S}_0 - \bar{S}_{+1}) + 2\bar{O}}{2}\right) / 2$$

where the bar superscript denotes the Echo Time Averaging described in more detail below.

The expression above, which describes the MeanRingingAverage from the third processing step can then be simplified to:

$$\bar{O} + \frac{2\bar{S}_0 - (\bar{S}_{-1} + \bar{S}_{+1})}{4}$$

As can be seen, the MeanRingingAverage includes some information about the formation. Specifically, it carries information about the change in formation signal—as represented by $\bar{S}$—over a depth interval comprising two PAPs. If $\bar{S}$ varies linearly with depth over the scale of two adjacent PAPs—three adjacent echo-trains at the same frequency—then the formation signal present in the MeanRingingAverage cancels out and the only component remaining is the non-formation signal, $\bar{O}$.

As an example of a practical case in which the formation signal disappears from the MeanRingingAverage, consider the situation at the boundary between two "thick" beds; where "thick" in this case means having a thickness greater than the antenna aperture of the tool. If $\text{CPMG}_{-1}$ and $\text{CPMG}_{+1}$ are measured one antenna aperture apart and straddling the boundary, then $\text{CPMG}_0$ will be the mean of the CPMG echo-trains above and below: In this case, $\overline{S}$ will vary linearly with depth and MeanRingingAverage will be given simply by $\overline{O}$. It should be noted that, in the preferred embodiment described above, the non-formation signal is assumed to be constant, having a value which may be a complex number.

While the preferred method described above uses two PAPs, it will be appreciated that there is no implied limitation on the maximum number of PAPs that could be used. Similarly, while the preferred method creates two Ringing Estimates, there is no implied limitation as to this number, since a single Ringing Estimate could be computed from a single PAP and can be used for the subsequent operations instead. It should also be apparent that more than two estimates can be formed at this time in alternative embodiments.

A1.b. Basic Ringing Estimate [DM]

In accordance with the direct measurement embodiment of the present invention, a Ringing Estimation Pulse Sequence (REPS) is used to determine directly the Basic Ringing Estimate. The Basic Ringing Estimate [DM] simply makes a separate measurement with a CPMG pulse sequence specifically designed to produce the ringing signal alone (designated as $\text{RING}_0$) without any other external or formation signal. In this case, Ringing$_0$, which is the ringing signal associated with the current sequence $\text{CMPG}_0$, is directly obtained from the CPMG sequence, using the expression:

$$\text{Ringing}_0(n) = \text{RING}_0(n) \qquad \text{Eqn. (2)}$$

In a preferred embodiment, the REPS sequence that can be used is a CPMG sequence without an initial $\pi/2$ pulse. It will be appreciated by those skilled in the art that such sequence will create an echo-train that contains no formation signal, but which contains the needed information to characterize the non-formation signals.

Accordingly, in a preferred embodiment the REPS is a short sequence (10 to 30 echoes) of $\pi$ pulses. The sequence is substantially identical to the CPMG sequence used in the standard measurement, except that it contains fewer 180 degree (i.e., $\pi$) pulses and no 90 degree pulse. That is, the REPS sequence should be a string of $\pi$ pulses with the same separation as in the following (or preceding) CPMG measurement sequence and the same pulse shape. Preferably, the sequence is run for every frequency used in the operation of the multi-frequency tool. Generally, REPS is run during the wait time between CPMG measurement sequences. The exact location depends on the activation being run as it depends on tool power/energy being available.

Figure 3:
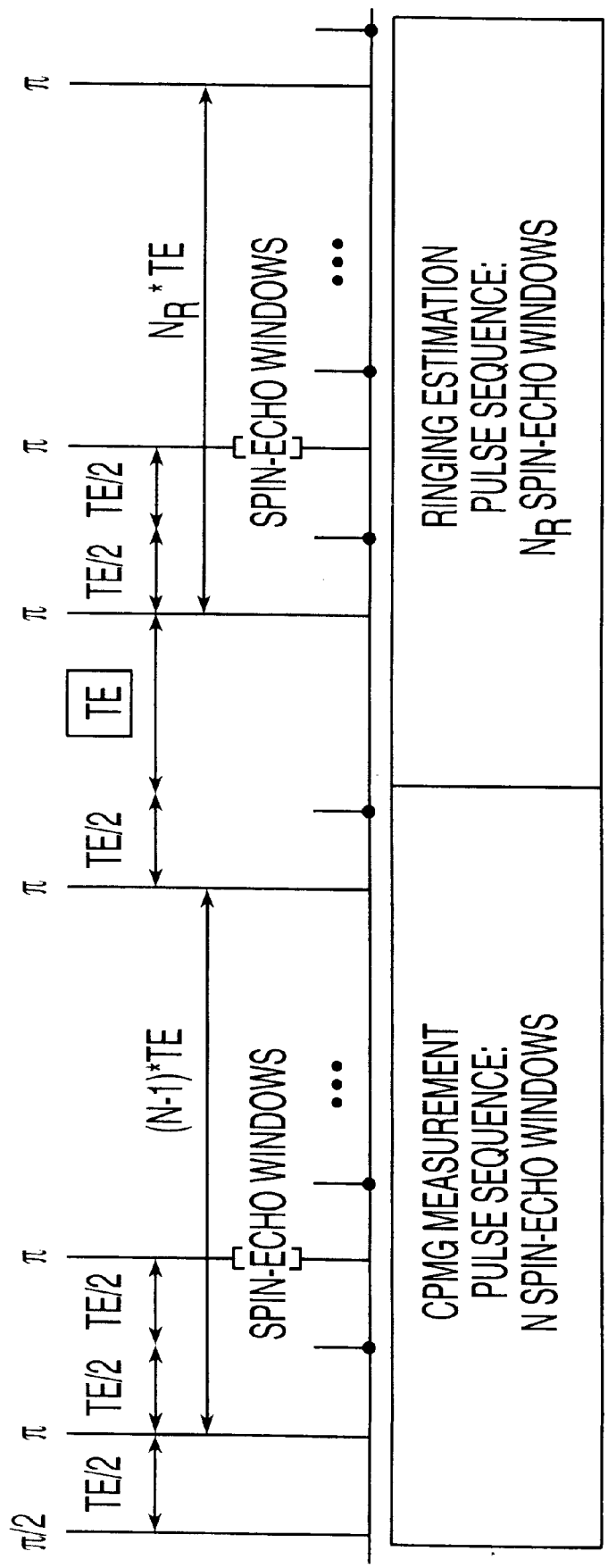
FIG. 3 is an illustration of a standard CPMG sequence along with a ringing estimation pulse sequence (REPS) used in a direct measurement of ringing signal contribution in accordance with a specific embodiment of this invention.
Figure 5D:
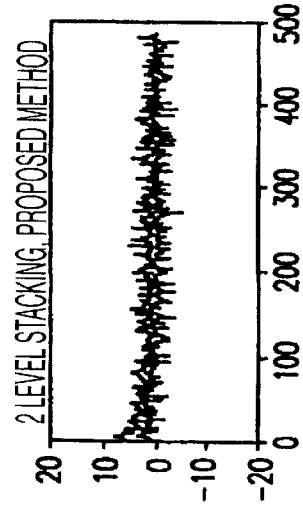
FIGS. 5A, 5B, 5C, 5D, 5E, and 5F (referred to herein collectively as FIG. 5) illustrate the effects of different levels of experiment stacking as applied in the Experiment Stacking step in accordance with the present invention.
Figure 5E:
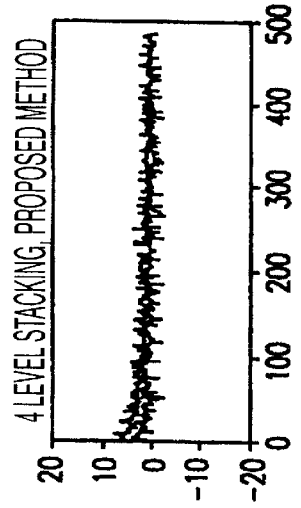
Figure 5F:
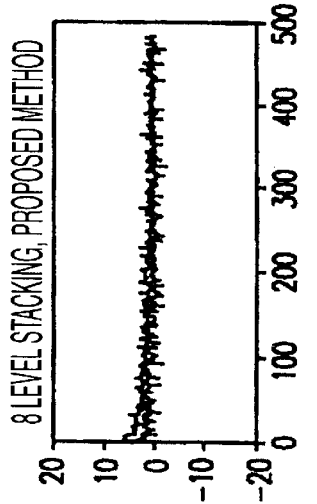
Figure 5A:
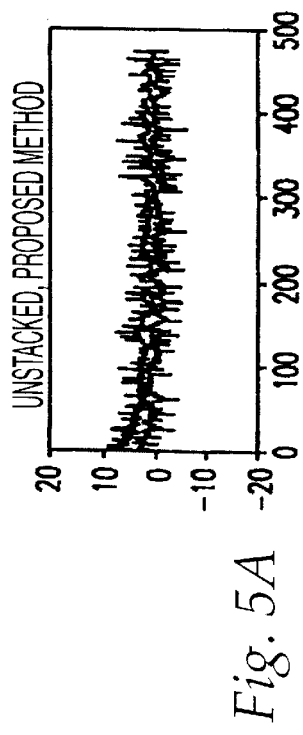
Figure 5B:
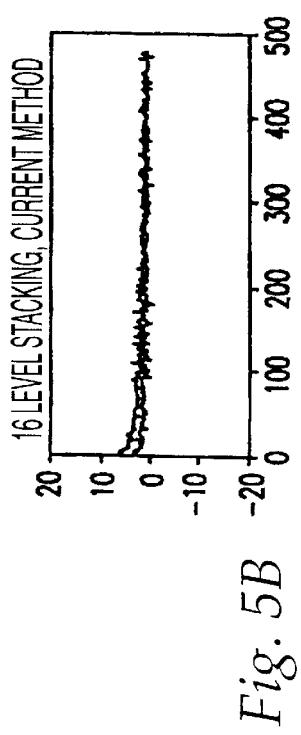
Figure 5C:
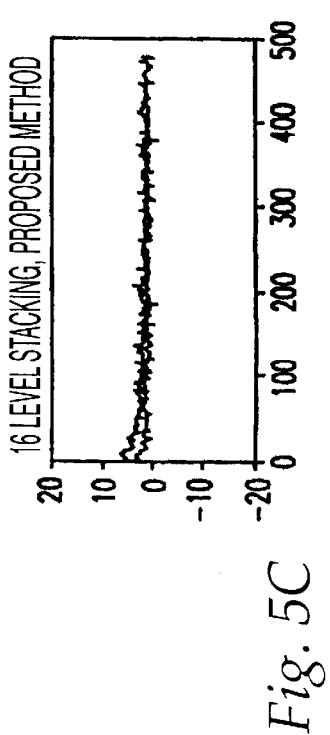
Figure 6:
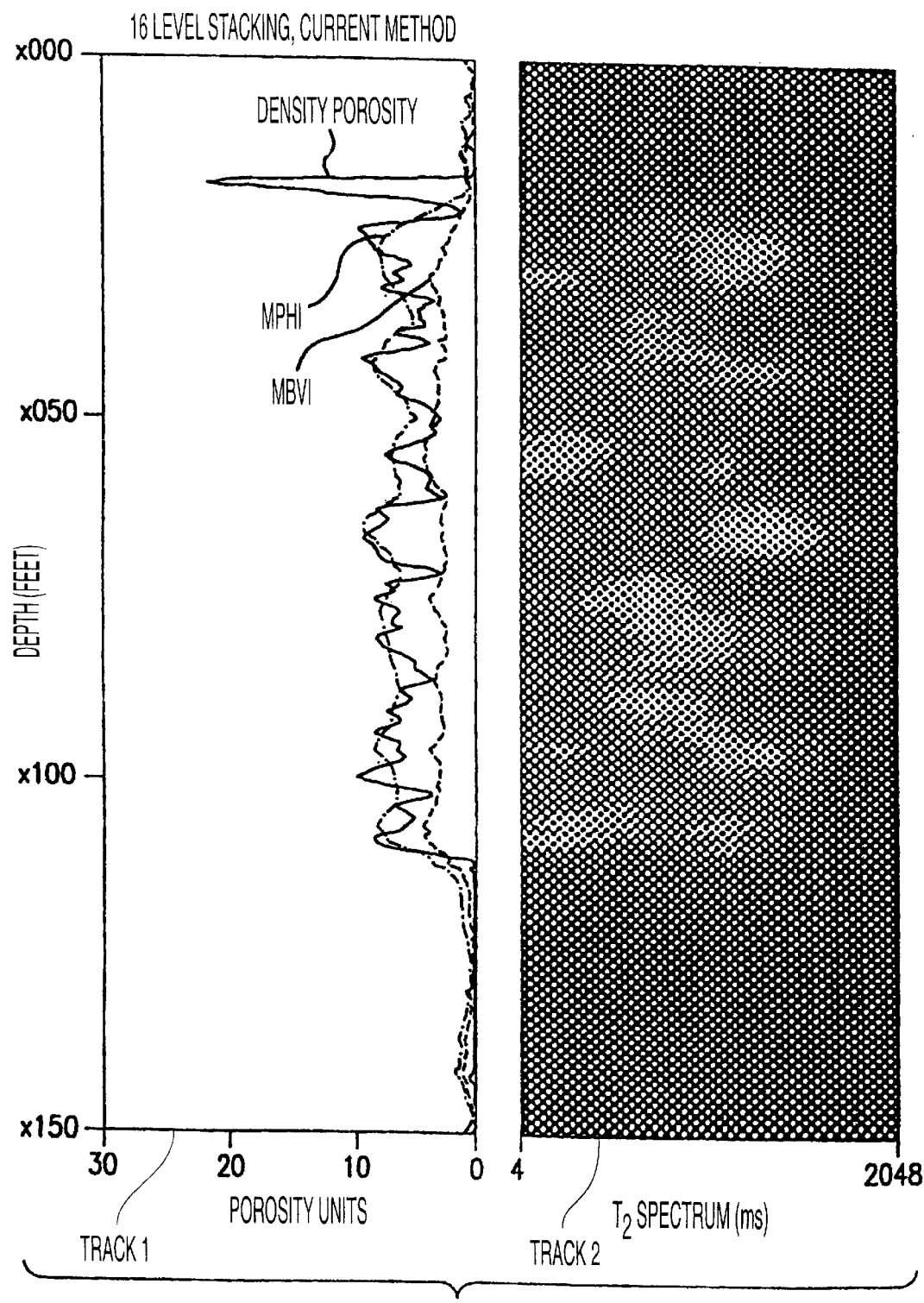
FIGS. 6 through 10 illustrate how different amounts of experiment stacking impact the vertical resolution of a section of log data in accordance with the present invention.
Figure 7:
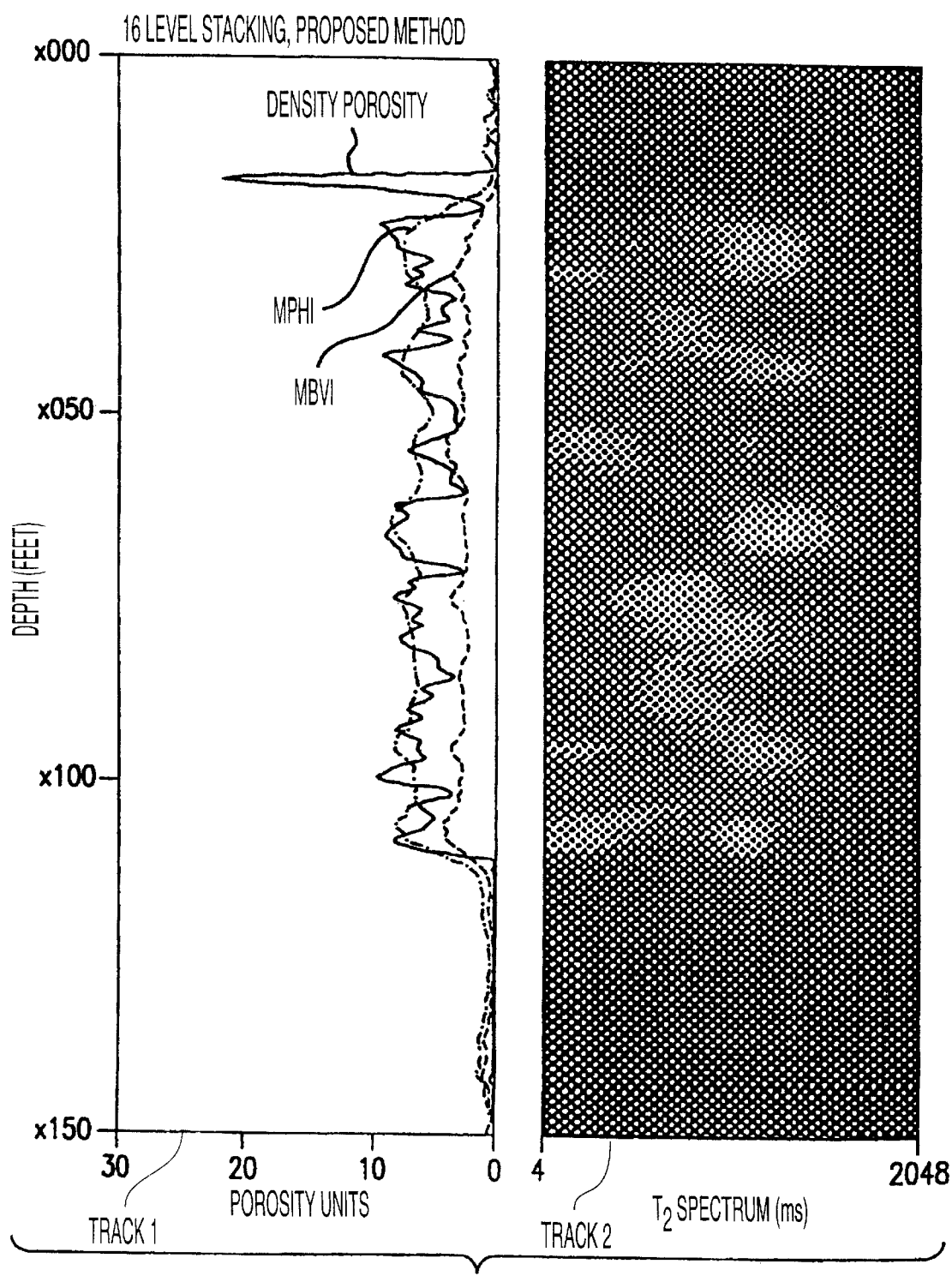
Figure 8:
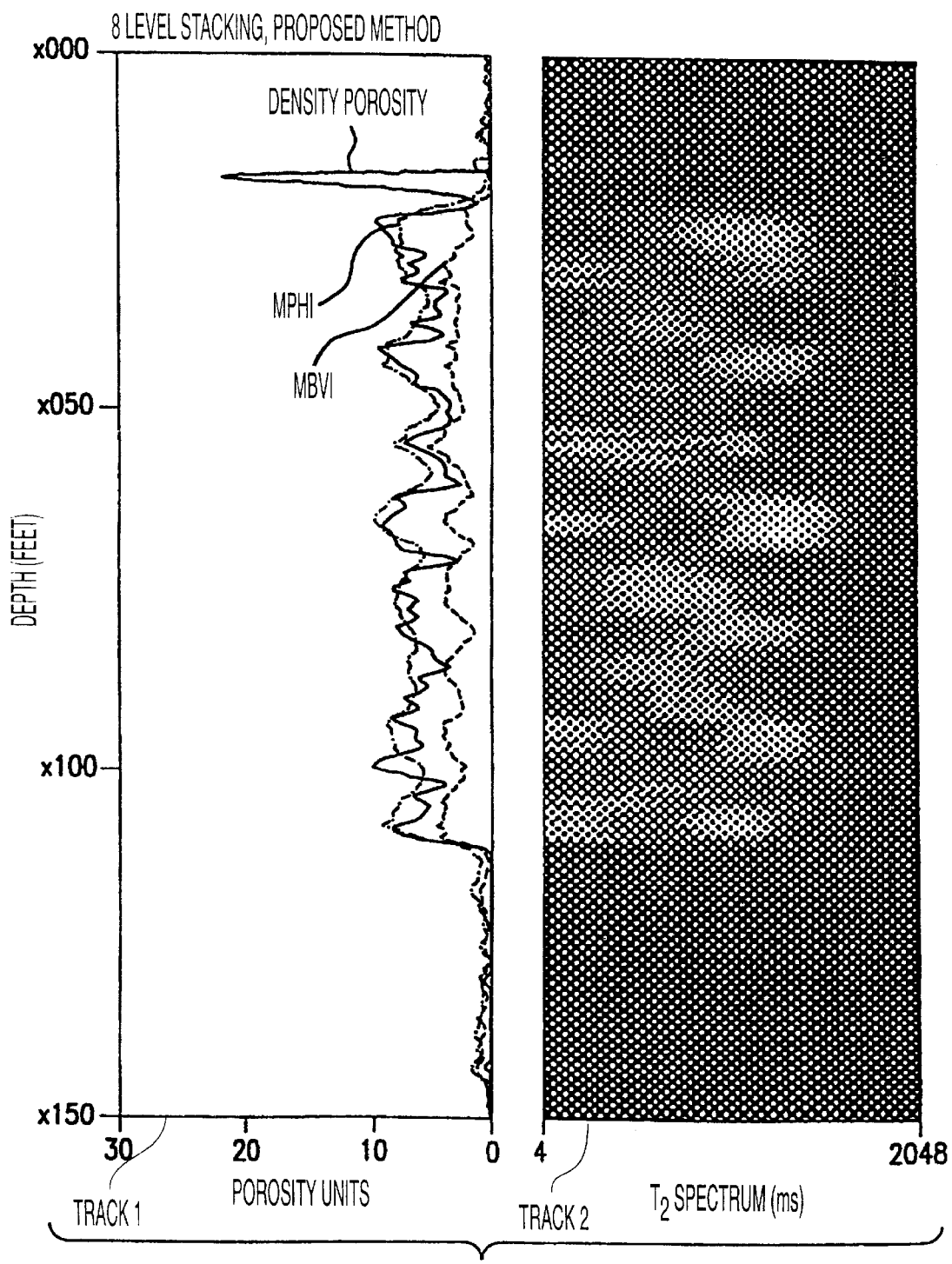
Figure 9:
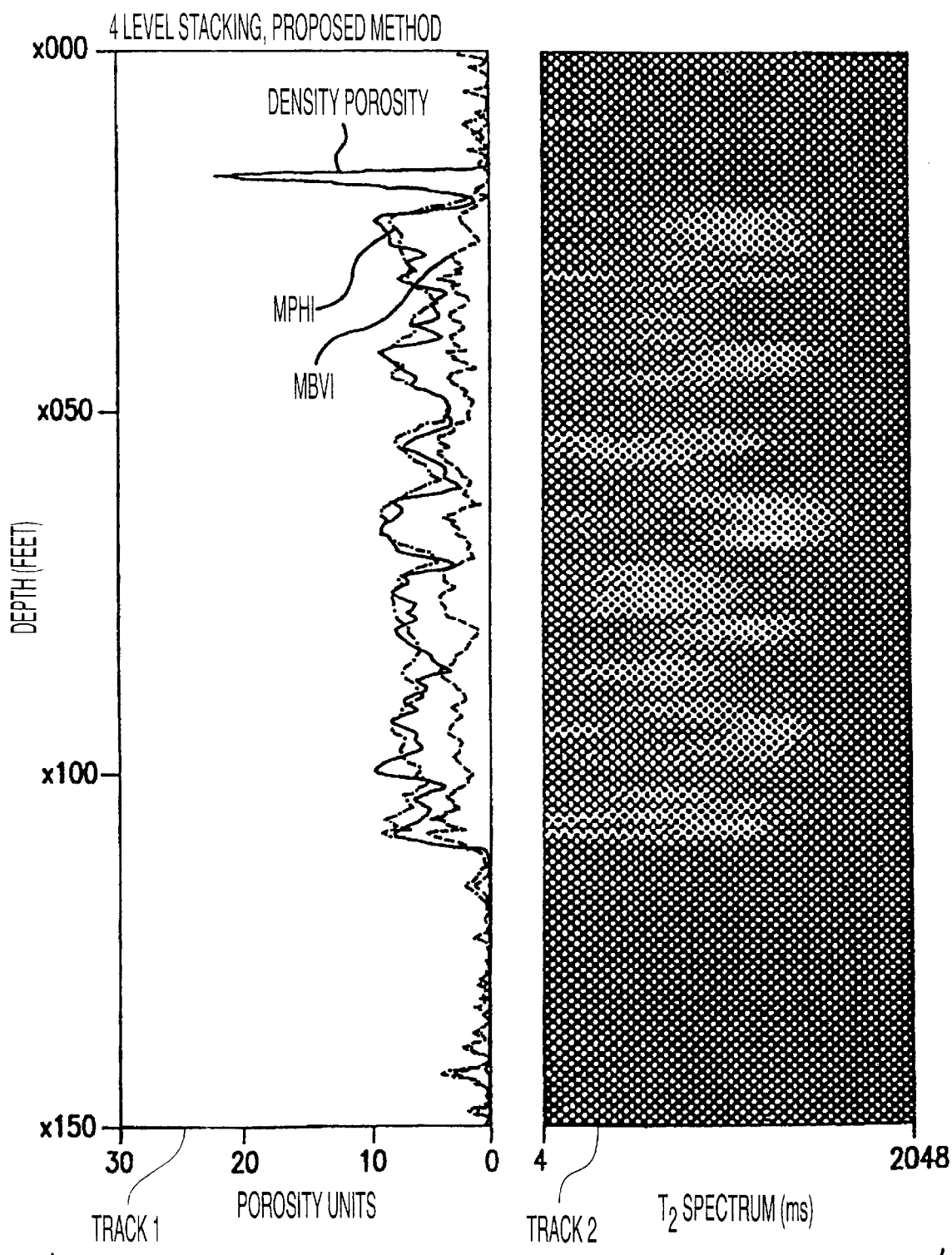
Figure 10:
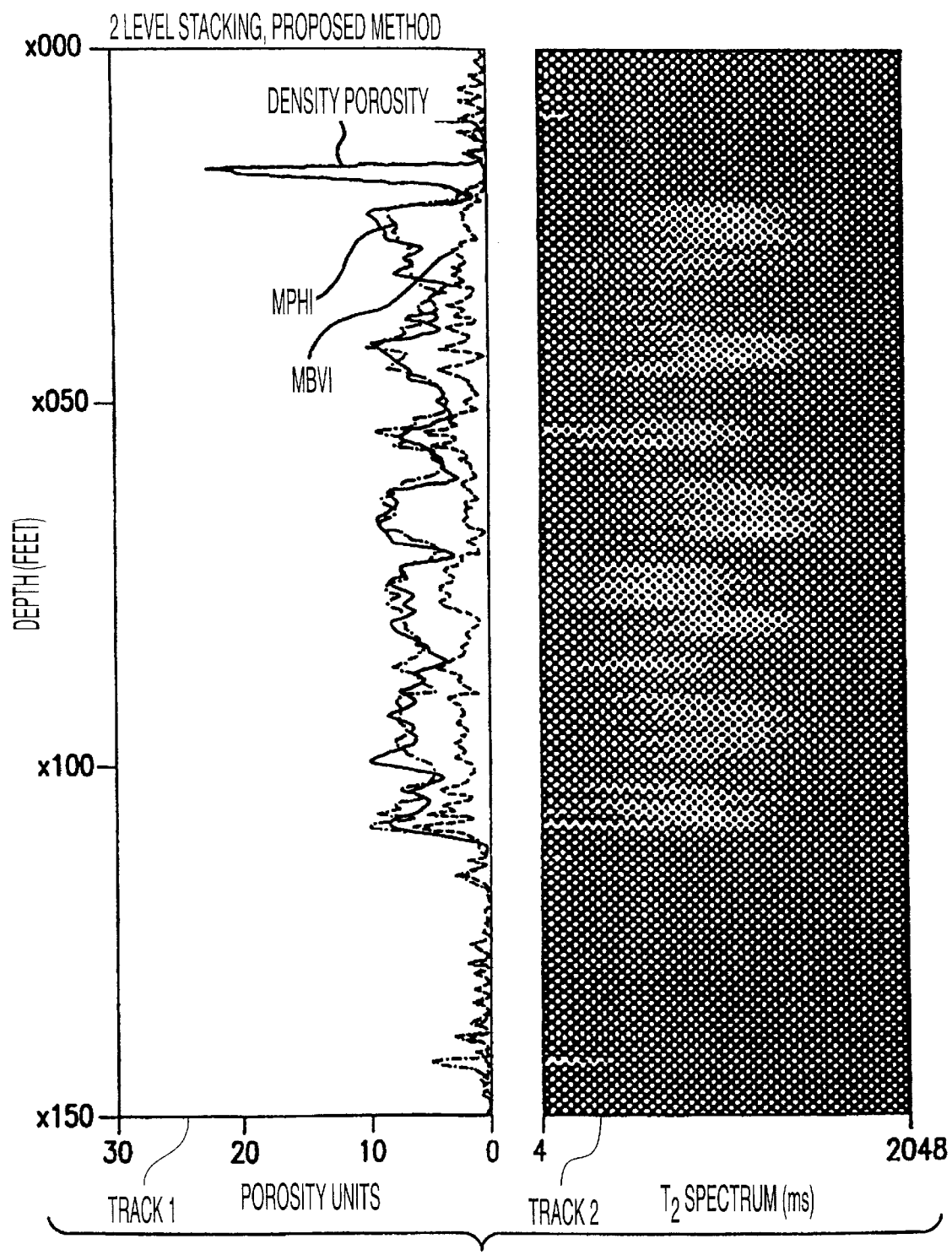
Figure 11B:
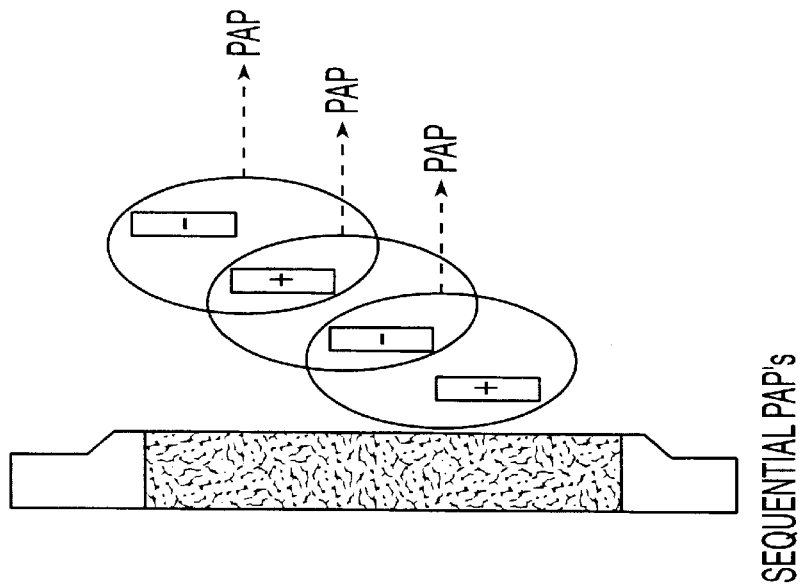
FIGS. 11A and 11B illustrate overlapping phase alternated pairs (PAPs) and sequential PAPs.
Figure 11A:
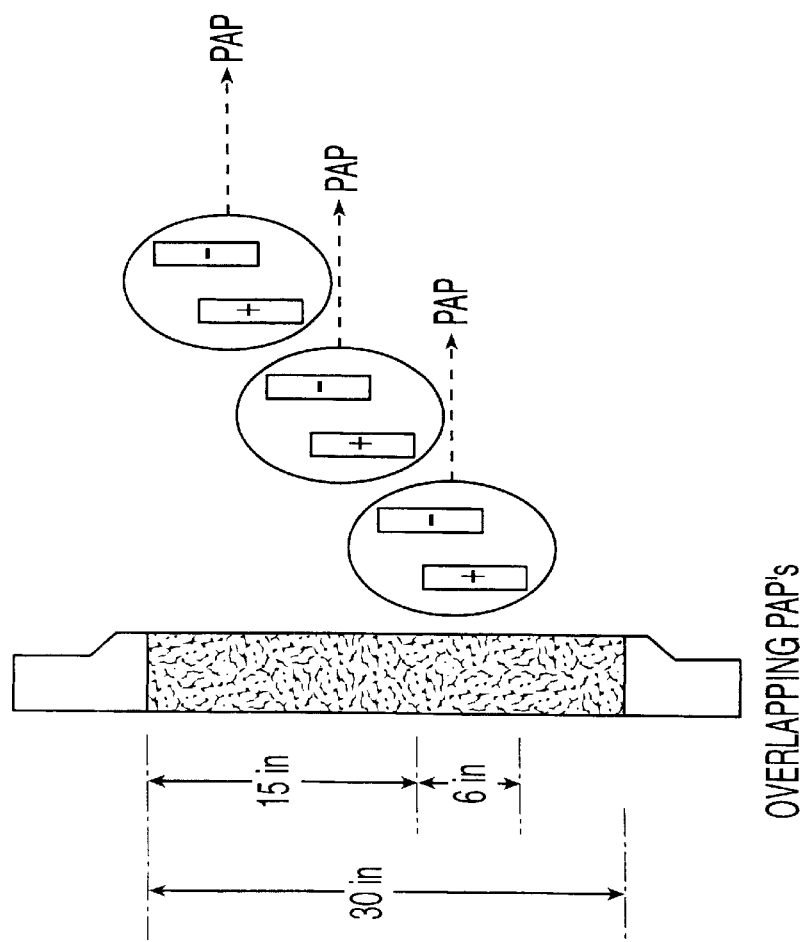

The REPS used in this embodiment of the invention is illustrated in FIG. 3. As shown, in the a timing diagram that illustrates an embodiment of a standard "CPMG Measurement Sequence"—presumably acquired after some build-up time $T_w$—followed by a "Ringing Estimation Sequence". Also shown in the drawings are the windows at which spin-echoes are acquired an interval $T_E/2$ after the $\pi$-pulses. As noted above, in the Ringing Estimation sequence, the measurements made in the spin-echo windows will actually be of the ringing signal and not of the formation spin-echoes.

The preferred embodiment shows the Ringing Estimation Sequence following the CPMG Measurement Sequence, with the first $\pi$-pulse occurring an interval $T_E$ after the last spin-echo window in the CPMG Measurement Sequence. The Ringing Estimation Sequence differs from the CPMG Measurement Sequence in that the first $\pi/2$-pulse is omitted, and in that the number of echoes in the Ringing Estimation Sequence (Nr) is not necessarily the same as the number of echoes in the CPMG Measurement Sequence (N). N and Nr are set according to the need to characterize separately the formation signal (N) and the ringing signal (Nr). It will be appreciated that in alternative embodiments of the invention the direct measurement sequence may precede the CPMG measurement sequence.

A.2. Echo Time Average

In accordance with the present invention, the Echo Time Average operation provides one or more mean ringing estimates. Broadly, the operation comprises calculating the average value of the basic ringing estimate vectors determined in the Basic Ringing Estimate operation described in Section A.1. above. In particular, in accordance with a preferred embodiment, the computation is mathematically expressed as follows:

$$\text{MeanRinging}_{-1} = \frac{1}{N} \sum_{n=1}^{N} \text{Ringing}_{-1}(n) \qquad \text{Eqn. (3)}$$

$$\text{MeanRinging}_{+1} = \frac{1}{N} \sum_{n=1}^{N} \text{Ringing}_{+1}(n)$$

In the event that the Basic Ringing Estimate [DM] method has been used, then only one summation is needed:

$$\text{MeanRinging}_0 = \frac{1}{N} \sum_{n=1}^{N} \text{Ringing}_0(n) \qquad \text{Eqn. (4)}$$

In the preferred embodiment expressed mathematically in Eqn. (3) and (4), all of the basic ringing estimate vector elements being used for calculating the average values are computed, yielding a single possibly complex number, which is an estimate of the contribution of non-formation, i.e., ringing signals. In the most general case it is unlikely that ringing will remain constant over the course of the NMR measurement or even over the course of a sequence. Accordingly, in alternative embodiments of this invention one or more subsets of the vector elements could be used instead, thereby generating a slowly developing complex function, which may be expected to more closely estimate the ringing phenomenon. It will be appreciated that if more than one subset is used, then MeanRinging will be cast as a complex-vector.

A.3. PAP Mean Ringing Average

In a preferred embodiment, the PAP Mean Ringing Average operation consists of combining one or more of the mean ringing estimates determined in the Echo Time Average Operation. This operation calculates the final estimated ringing level by calculating the mean of the separate mean ringing estimates, expressed mathematically as follows:

$$\text{MeanRingingAverage} = \qquad \text{Eqn. (5)}$$
$$\frac{\text{MeanRinging}_{+1} + \text{MeanRinging}_{-1}}{2}$$

In the event that the Basic Ringing Estimate [DM] method has been used, then MeanRingingAverage is identical to MeanRinging$_0$. In the event that MeanRinging is a complex-vector, then the method for computing MeanRingingAverage results in a complex-valued vector.

In accordance with the present invention, it has been found that the assumption of a constant ringing signal is more closely matched if the following condition is met:

$$T_E * f = N$$

i.e., when the product of the echo spacing ($T_E$) in milliseconds and the operating frequency (f) for the CPMG spin echo train(s) is an integer number N.

In addition to the preferred method(s) described above, other alternative methods for performing the Ringing Estimation step can be used and include, but are not limited to:

(a) Using just a single PAP that incorporates the current primary CPMG;

(b) Using more than single Phase Alternate Pair CPMGs both preceding and following the current primary CPMG;

(c) Using one or more PAPs or other combinations of echo-trains that may or may not incorporate the primary current CPMG;

(d) Making intermediate ringing level estimates and then using other filters, or means of characterization, to determine the final estimated ringing level;

(e) Making intermediate ringing level estimates and then characterizing any depth-dependent behavior of the ringing level estimates to determine the final estimated ringing level.

Using the principles of this invention outlined above, computation of the Ringing Estimates using the above alternative methods can be derived by persons of average skill in the art, and will not be considered in further detail. Other methods or variations of the Ringing Estimate processing step will be apparent to those skilled in the art and are intended to be used, where applicable.

B. Ringing Elimination

In accordance with the present invention, the estimated level of ringing (a single number or slowly varying function) obtained in the previous step and described in Section A above is next removed in the step of Ringing Elimination from the current CPMG echo-train measurement. This ringing elimination is accomplished in accordance with a preferred embodiment by subtracting the estimated ringing from each and every echo of the current measurement CPMG echo train, as expressed below:

$$CPMG_0'(n) = CPMG_0(n) - MeanRingingAverage \qquad \text{Eqn. (6)}$$

Again, since the CPMG echo train and the estimated ringing have both a real and imaginary component, the ringing elimination is performed for both the real and imaginary channels.

C. Experiment Stacking

Experiment stacking is used in accordance with the present invention in order to improve the signal-to-noise ratio (SNR) to an adequate level. It should be noted that for multi-frequency tools, such as the MRIL Prime tool, this step means that the experiment stacking is performed across one or more frequencies depending on how the data was acquired.

Experiment stacking is employed in accordance with the present invention in two embodiments. In a first embodiment, the method uses a boxcar running average filter, whose length depends primarily on the desired signal-to-noise. It will be appreciated by those of skill in the art, that using filters with no other length constraints is a distinct improvement over the prior art, where the filter length is calculated as a multiple of the number of frequencies and phase alternate pairs (PAPs). Therefore, where the data dictates it, in accordance with the present invention on can use a boxcar filter of length 10, whereas in prior art stacking one would have to use a filter of length 16, which introduces processing delays and may lead to decreased vertical resolution of the data.

In a preferred second embodiment, instead of using a boxcar filter for the Experiment Stacking step other types of filters can be used advantageously and may be more appropriate for achieving the desired signal-to-noise ratio. For example, the filters described below in Section D provide an alternative to boxcar filtering to improve the vertical resolution of NMR logs such as those obtained by the MRIL tool.

In accordance with a preferred embodiment, all three steps discussed in Sections A, B and C above can be performed as a single pass through the acquired data, CPMG by CPMG, typically in a successive or chronological fashion. In an alternative embodiment, the first two steps can be performed in a single pass through the acquired data in a successive fashion, with the third step performed as a second pass.

Post-Processing

After Experiment Stacking, which in accordance with this invention is the last pre-processing step, stacked CPMG echo trains can be treated in the same fashion as the stacked CPMG echo trains that result from prior art methods: for example, the stacked echo-trains could be "phase-rotated", and then "inverted in the $T_2$ domain" to obtain the "$T_2$ spectrum" of the echoes, as known in the art. The interested reader is directed to the disclosure of U.S. Pat. No. 5,517,115, as well as U.S. Pat. Nos. 5,212,447; 5,280,243; 5,309,098; 5,412,320; 5,557,200 and 5,696,448 for a detailed description of these methods.

Proposed Method: Special Case

The proposed method can, optionally, be altered in those circumstances in which the Experiment Stacking requires stacking echo-trains across PAPs. In this case, the Ringing Estimation and Ringing Elimination steps can be accomplished by taking the PAP differences—as is done in the current method—and then applying the appropriate type of Experiment Stacking. This approach is further addressed in Section D below.

EXAMPLES

FIG. 4 shows graphically the results of the first and second processing steps discussed above. For all plots, the x-axis is the echo time and the y-axis is the echo or ringing amplitude, the real channel echo amplitudes are shown in red and the imaginary channel amplitudes are shown in green. (color drawings attached, as well as black and white).

The first column, with three plots (FIGS. 4A, 4B, and 4C), shows the input primary phase CPMG echo train ($CPMG_0$) in the middle plot (FIG. 4B). The input alternate phase CPMG echo train following the primary phase ($CPMG_{+1}$) is shown in the upper plot (FIG. 4A) and the input alternate phase CPMG echo train preceding the primary phase ($CPMG_{-1}$) is shown in the lower plot (FIG. 4C).

The second column with two plots (FIGS. 4D and 4E) shows the intermediate estimated ringing level results from Step 1a: $Ringing_{+1}$ in the upper plot (FIG. 4D) and $Ringing_{-1}$ in the lower plot (FIG. 4E). In addition the intermediate estimated ringing level results are shown as the horizontal lines in the respective plots: $MeanRinging_{+1}$ in the upper plot (FIG. 4D) and $MeanRinging_{-1}$ in the lower plot (FIG. 4E); with the magenta line (the lower line) representing the real component and the cyan line (the upper line) representing the imaginary component.

The third column plot (FIG. 4F) shows the end of the ringing removal step for the current primary phase CPMG echo train where the final estimated ringing levels (MeanRingingAverage) from the Ringing Estimation step have been removed from the input primary phase CPMG echo train.

FIG. 5 shows the effects of different levels of experiment stacking as would be applied in the Experiment Stacking step. For each plot one track (in red color—that is, the lower line, starting from the left) shows the real channel and the other track (in green color—that is, the upper line, starting from the left) shows the imaginary channel.

The plot at the top of the first column (FIG. 5A) is identical to the last plot in FIG. 4 (i.e., FIG. 4F). The middle and bottom plots of the first column (FIGS. 5B and 5C, respectively) show that the method of this invention provides almost identical results as the prior art method does when the same amount of experiment stacking (16 levels) is used.

The second column (FIGS. 5D, 5E, and 5F) shows how the signal-to-noise of the resulting CPMG echo trains improves with increased amounts of experiment stacking.

FIGS. 6 through 10 show how different amounts of experiment stacking impact the vertical resolution of a section of log data. In particular, Track 1 shows a Density Porosity curve in black—computed from a Bulk Density log assuming grain and fluid densities of 2.65 and 1.0 gm/cc respectively—the MRIL Effective porosity (MPHI) in magenta and MRIL Bulk Volume Irreducible (MBVI) in red. Track 2 shows the T2 distribution resulting from the MAP inversion algorithm.

The illustrative examples show that vertical resolution improves as the level of experiment stacking decreases with a corresponding trade-off of reduced accuracy of the inversion results. The accuracy reduction can be acceptable to a point the user is comfortable with, which then sets the acceptable vertical resolution for any particular data set.

D. Alternatives to Box-Car filtering

Described below are approaches for improving the vertical resolution of NMR logs by replacing the box-car filter used in the prior art for removing both coherent and random noise signals, with a combination of two filters, in which the above functions are advantageously separated. A particular problem addressed below is that since in multi-frequency tools any two PAPs are separated by N CPMG pulse sequences, where N is the number of operating frequencies, the filter length used in the prior art has to be a multiple of 2*N. Due to this limitation, very long filters have to be used in the prior art, especially when the number N of operating frequencies is high. For example, there are N=8 operating frequencies that can be used in a MRIL tool, so if full use is made of these frequencies, the minimum filter length is 16. Due to relatively low signal levels and the corresponding need for signal stacking, filter lengths of 64 are not uncommon.

D.1. Prior Art Filtering

The current processing practice involves the use of boxcar (BC) filters, which simultaneously perform phase alternated pair (PAP) stacking for coherent noise removal, and signal averaging for random noise reduction. The filter lengths used to this end are referred to as the Running Average (RA), and are multiples of the so called Minimum Running Average (MRA). As known in the art, the MRA depends on the type of the tool and its activation (i.e., dithered vs. non-dithered). The minimum filter lengths for the BC filters, for both MRIL-C and MRIL-Prime tools are shown in the following Table 1.

TABLE 1

Minimum Running Averages (MRA) for MRIL-C, and MRIL-Prime Tools

| Tool | No. of Freq. | Dithering | MRA |
| --- | --- | --- | --- |
| MRIL-C | 2 | No | 4 |
| MRIL-C | 2 | Yes | 8 |
| MRIL-Prime | 8 | No | 16 |

In general, the filter length, or running average RA, is determined by $\sigma_n$, which is the standard deviation of the noise. The proper running average filter length is defined as RA=n·MRA that results in $\sigma_n=1$, where n is an integer number. Although BC filters are efficient, primarily because of the simultaneous treatment of coherent and random noise components, and are easy to implement, there are four general problems associated with their use in practical applications.

First, in most high-gain environments (oil based mud, 8.5-inch hole, high frequency operation, etc.), the RA that results in $\sigma_n \approx 1$ can be as low as 4. However, the actual running average used in such cases is typically larger due to the MRA condition. For example, consider a high-gain case, where RA=4 would be sufficient. The actual running average to be used, however, has to be 16 for the MRIL-Prime tool, or 8 for a dual-frequency MRIL-C tool (4 if the activation is not dithered).

Next, the constraint that the RA must be a multiple of MRA, results in a similar problem, particularly for tools such as the MRIL Prime tool. For example, consider the case of a MRIL Prime measurement, where RA=24 would actually satisfy the $\sigma_n \approx 1$ condition. Since MRA is 16 for the MRIL Prime tool, an RA value of 36 must be used instead of 24.

Further, the boxcar filter has an equal-weight distribution, which causes significant degradation of vertical resolution in those cases where a large number of CPMGs must be stacked for proper random noise cancellation. Consider, for example, a very highly conductive mud, where RA=48, and the sampling rate is 2 CPMGs per foot. In this case, a single point on the porosity log represents a formation volume thickness of 24 feet, and a bed near the edge of the sampled volume has equal weight in the porosity as a bed just at the mid-point.

Figure 12:
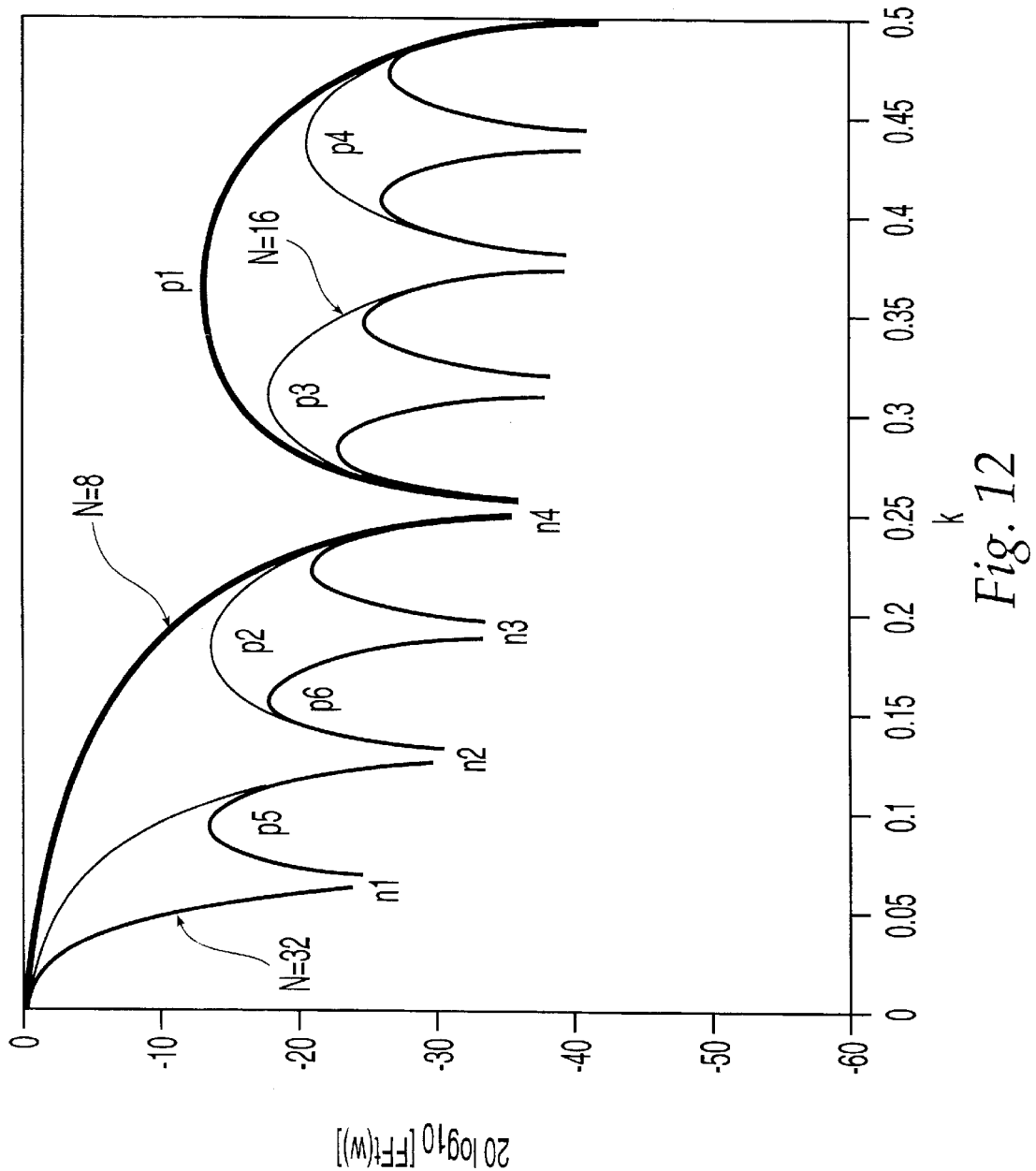
FIG. 12 illustrates the frequency response of several boxcar filters, which are used in the prior art methods.

Finally, the output of the boxcar filter is generally very noisy. The frequency response of several boxcar filters can be seen in FIG. 12. Notable in the figure is the presence of many notches in the frequency response, as well as the numerous secondary peaks. In practical applications these notches, in addition to the secondary peaks, cause oscillatory and noisy behavior. Further, one can note the secondary peaks, marked in FIG. 12 as p1 to p6. These peaks generate noise, since they are at or above −20 db level, which is considered the detection threshold for human eye.

D.2. An Alternative Approach

In accordance with the present invention an alternative approach is proposed that eliminates problems associated with the prior art. It is perceived that the main problem with the BC filter (in addition to its noisy behavior for large N) is its equal-weight distribution; as noted above, depending on the length of the filter local features may be lost. In accordance with the present invention it is proposed to use a tapered filter, such as the Hamming filter, which generally results in better preservation of the local features.

Unfortunately, however a tapered filter alone cannot deal with the coherent noise components, due to the very nature of the MRIL data acquisition in multi-frequency mode. Thus, in accordance with the present invention removal of the coherent non-formation signals must be performed prior to the application of a tapered filter. The prior art discloses the use of PAPs to this end. The disclosure in Sections II.A/B and C this application illustrate other ways of removing this undesirable signal component.

In contrast to the simultaneous treatment of coherent and random noise by the boxcar approach, use of a tapered filter requires a two step approach, where PAPs-type processing to remove coherent noise signal components is followed by a tapered filter, as explained below.

Figure 13A:
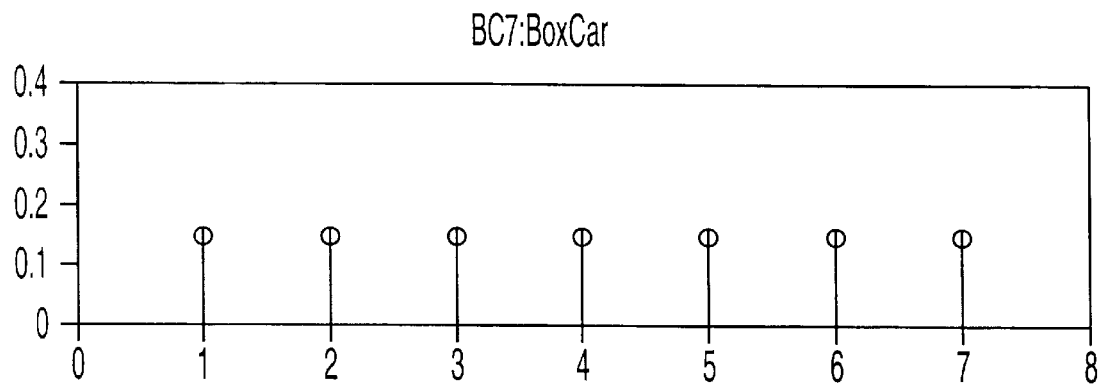
FIGS. 13A, 13B and 13C are plots of the filter coefficients of the box-car (A), Comb filter (B), and a Hamming filter (C)
Figure 13B:
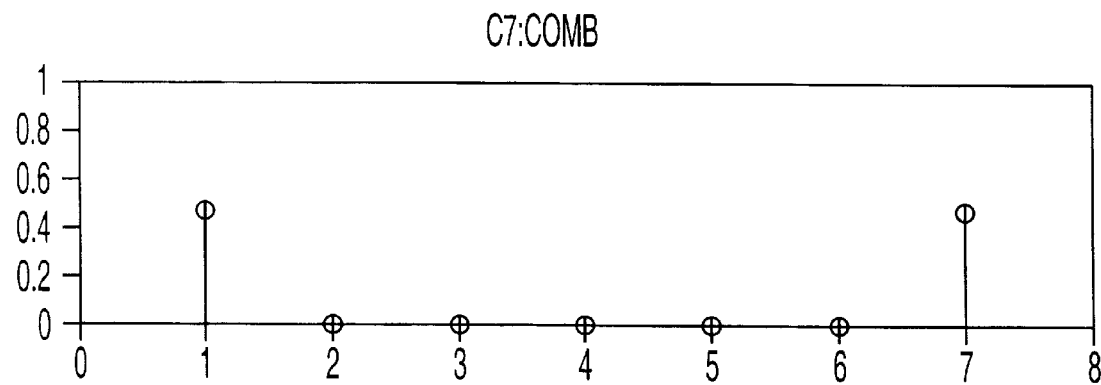

First, a Comb filter of length n (Cn) is applied to perform removal of the coherent noise components. A plot of the box-car and a Comb filter, for N=7, can be seen in FIGS. 13A and 13B. The filter lengths for the Comb filter depend on the tool and its activation type, and are listed in Table 2 below. Note that in this approach each CPMG sequence that belongs to a particular frequency is combined with its true phase alternated pair. CPMGs from other frequencies are not involved in this operation.

TABLE 2

Comb filter lengths for MRIL-C, and MRIL-Prime Tools

| Tool | No. of Freq. | Dithering | MRA |
| --- | --- | --- | --- |
| MRIL-C | 2 | No | 3 |
| MRIL-C | 2 | Yes | 5 |
| MRIL-Prime | 8 | No | 9 |

Figure 13C:
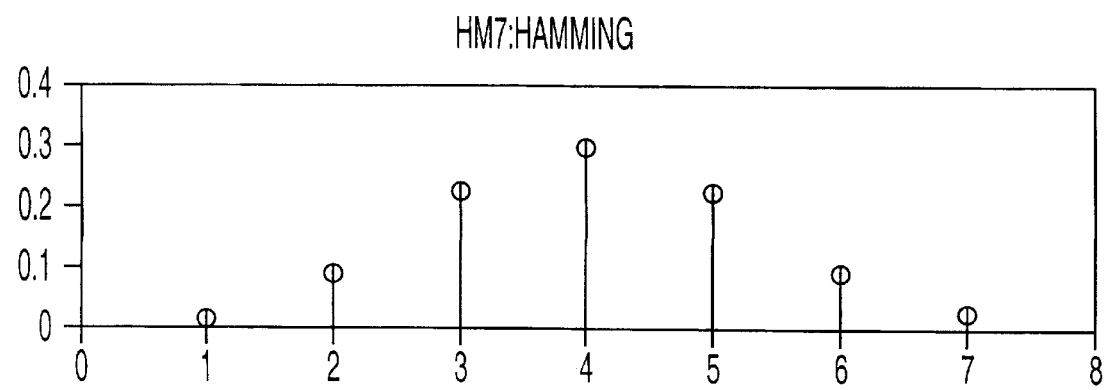

Secondly, a tapered filter of length n, such as a Hamming filter (HMn), is applied to the already phase alternated CPMGs, as shown in the illustrative examples below. This operation preserves more of the local information, while reducing random noise. A Hamming filter is illustrated in FIG. 13C.

While the definitions of these filters are well known in the art, they are repeated next for convenience.

For all the filter definitions given below, N is the number of the filter elements, where it is assumed that they run between $1 \leq i \leq N$. Information on other tapered filters can be found in standard signal processing references, such as "Handbook for Digital Signal Processing", Edited by Sanjit Mitra and James Kaiser, Wiley & Sons, Inc. 1993. The content of this reference relevant to filter design is hereby incorporated by reference for background.

1. BCn. BoxCar filter with N points. The filter coefficients are given by $$f_i = \frac{1}{N}$$

2. Cn. Comb filter with N points. The filter coefficients are given by $f_i$=0.5 for i=1 and i=N 0.0 otherwise 3. HMn. Hamming filter with N points. The filter coefficients are given by $$f_i = 0.54 - 0.46 \cos\left[\frac{2\pi(i-1)}{N-1}\right]$$

The overall effect of the Comb filter and the tapered filter can be analyzed by considering the Fourier transform of their convolution. Comparison of the current and proposed methodologies based on their Fourier transforms is illustrated below. It should be noted that Filter 1 and Filter 2 in accordance with this invention need not necessarily be separate and distinct entities—in specific implementations they could be built into a single filter that has the response corresponding to the convolution of the two separate filters. For reasons of conceptual simplicity, the two filters are considered as being separate in the sequel.

Filter Response Comparison

Assume a hypothetical case where 16 CPMGs must be stacked to satisfy the $\sigma_n \approx 1$ condition. The response of the proposed approach in accordance with the present invention is compared to the response of the conventional boxcar filter in three separate cases simulating:

1. Dual-frequency MRIL-C, non-dithered activation (C3HM16),
2. Dual-frequency MRIL-C, dithered activation (C5HM16),
3. MRIL-Prime (C9HM16).

Case 1: BC16 vs. C3HM16

Figure 14:
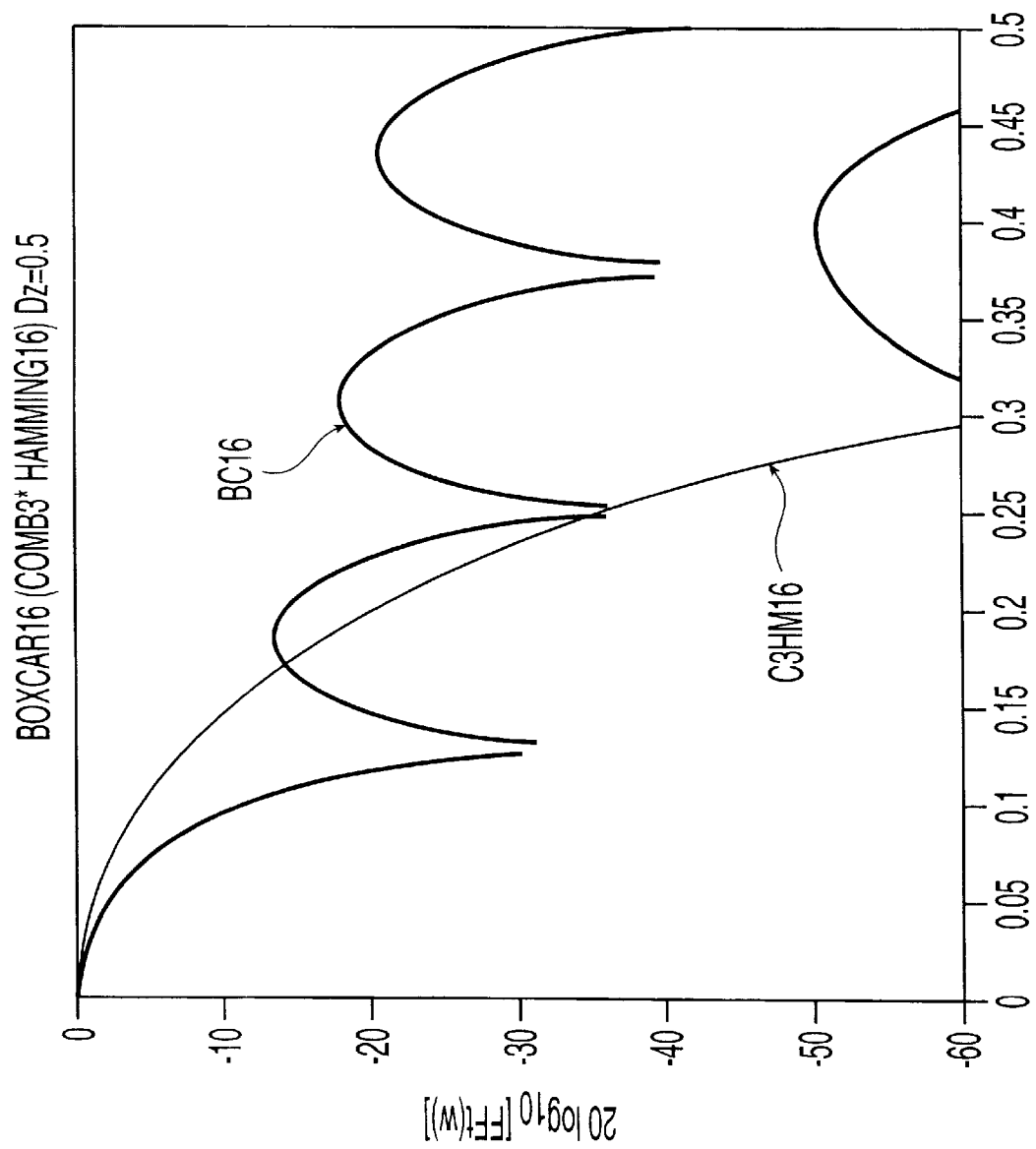
FIGS. 14 through 18 illustrate comparisons between the frequency response of box car filters used in the prior art with combination filters used in accordance with the present invention.

In the case of a dual-frequency MRIL-C tool, with a non-dithered activation, a Ccomb filter of length 3 is followed by a Hamming filter of length 16. The comparison of BC16 vs. C3HM16 is given in FIG. 14. As shown, the BC16 filter has a notch at k=0.125, and two peaks at k=0.175, and k=0.32, all generating noise in a visible range. The C3HM16 filter on the other hand monotonically decreases, has no significant notches, or secondary visible peaks. There is a significant improvement in the vertical resolution, with almost no side-lobe noise.

Case 2: BC16 vs. C5HM16

Figure 15:
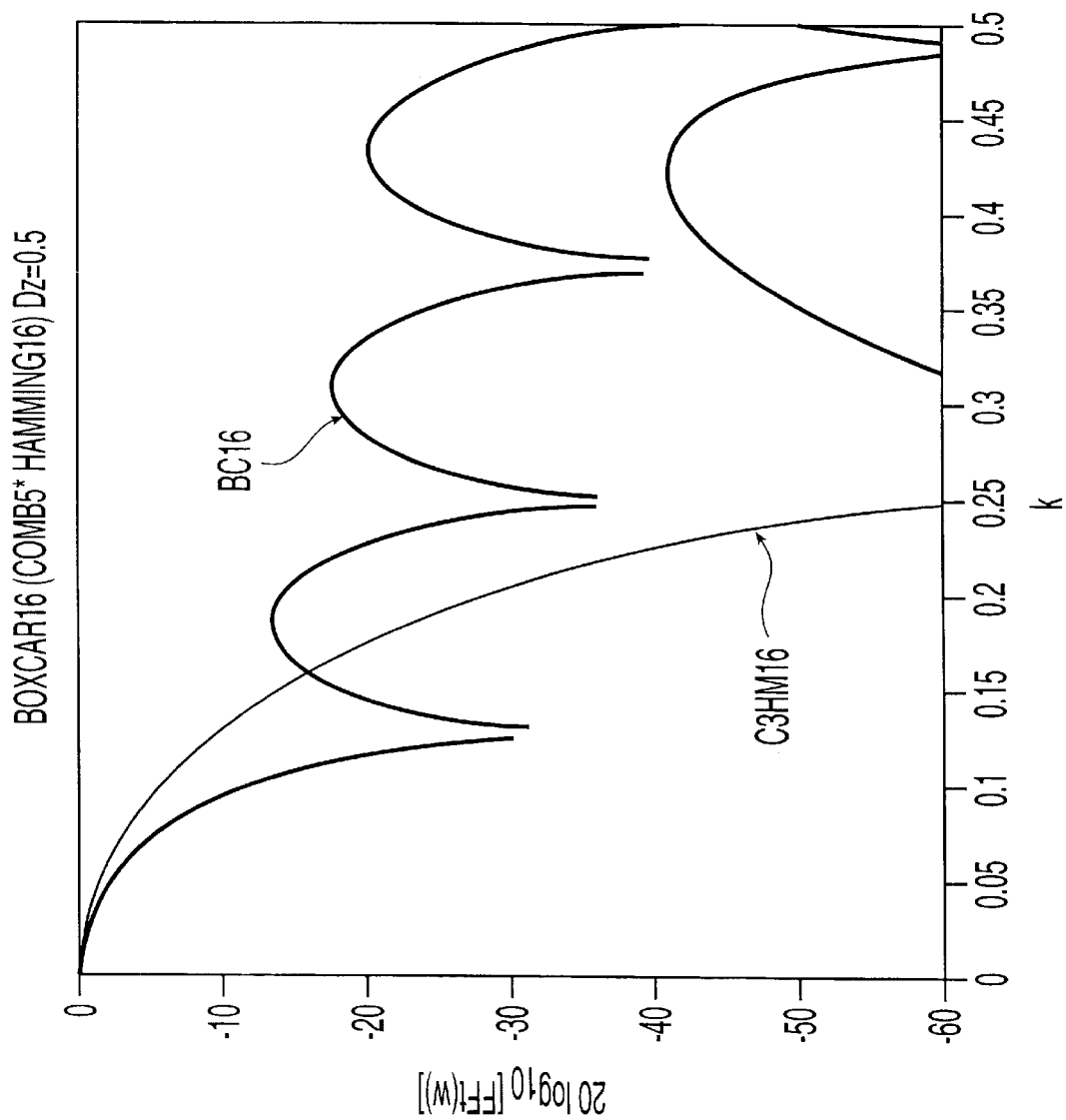

In the case of a dual-frequency MRIL-C tool with dithered activation, a comb filter of length 5 is followed by a Hamming filter of length 16. The comparison of BC16 vs. C5HM16 is given in FIG. 15. The C5 HM16 filter decreases monotonically, as in FIG. 14. Although the boxcar filter may appear to contain a larger proportion of the wavelengths around k=0.18, the notch followed by a peak causes oscillations in the logs. The first notch of the C5HM16 filter occurs at a later spatial-frequency, improving vertical resolution, and the following side-lobe is much smaller compared to the boxcar filter, resulting in significantly reduced side-lobe noise.

Case 3: BC16 vs. C9HM16

Figure 16:
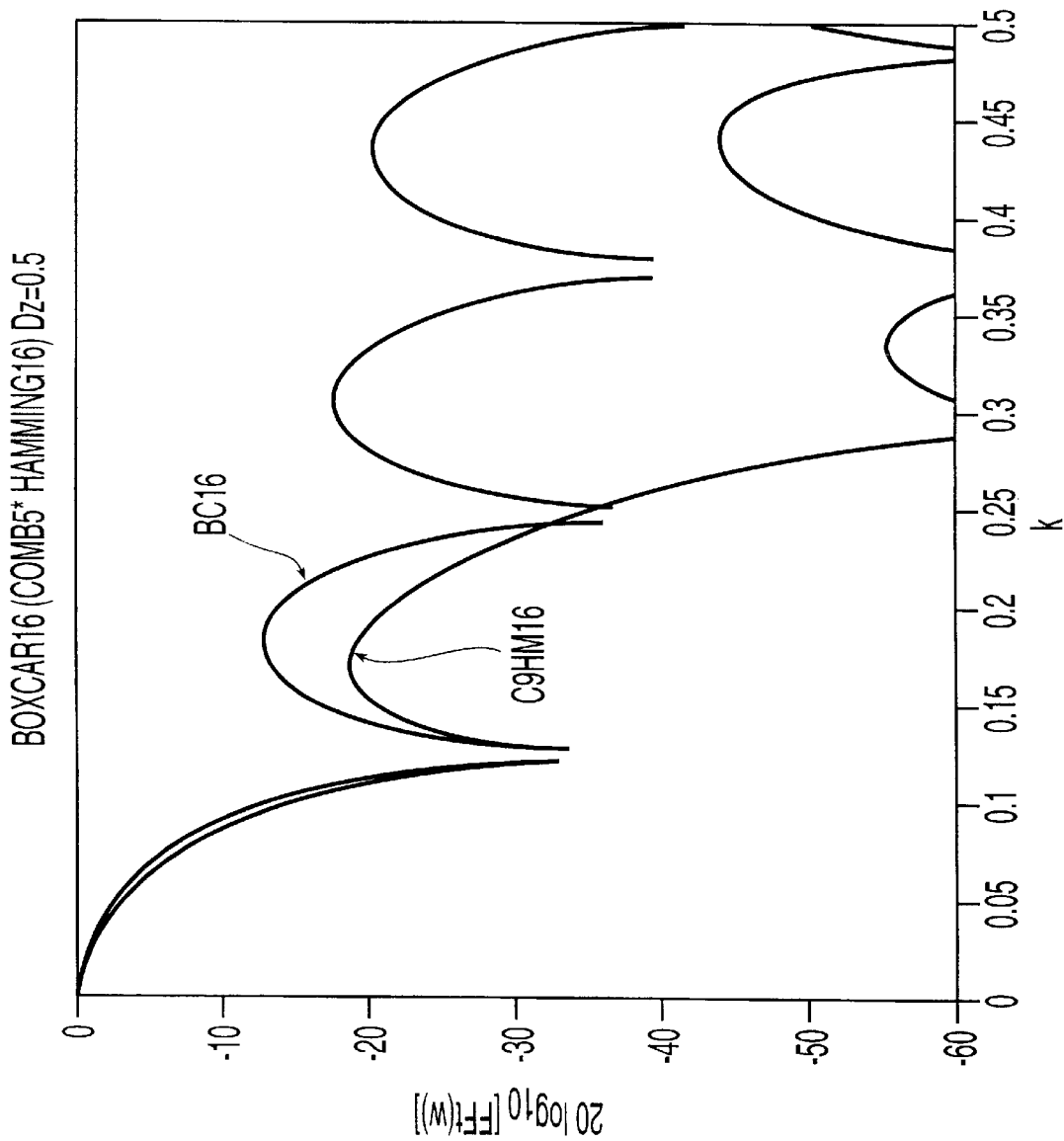

In the case of an MRIL-Prime tool, a comb filter of length 9 is applied before a Hamming filter of length 16. The comparison of BC16 vs. C9HM16 is given in FIG. 16. Both filters have similar responses up to the first notch, explaining why the proposed method may not improve vertical resolution in this particular instance. However, the C9HM16 filter generates a less-noisy response (by approximately 6 dB), since its main side-lobe is weaker compared to the BC16 filter. The second peak of the C9HM16 filter is not as strong as that of the BC16. Although this may imply better resolution on the part of the BC16 filter, the stronger second peak is actually a source of noise that can be observed on the logs. The more suppressed second peak of the C9HM16 response results in a cleaner response.

Filter Response Comparison for Longer Filter Lengths

Figure 17:
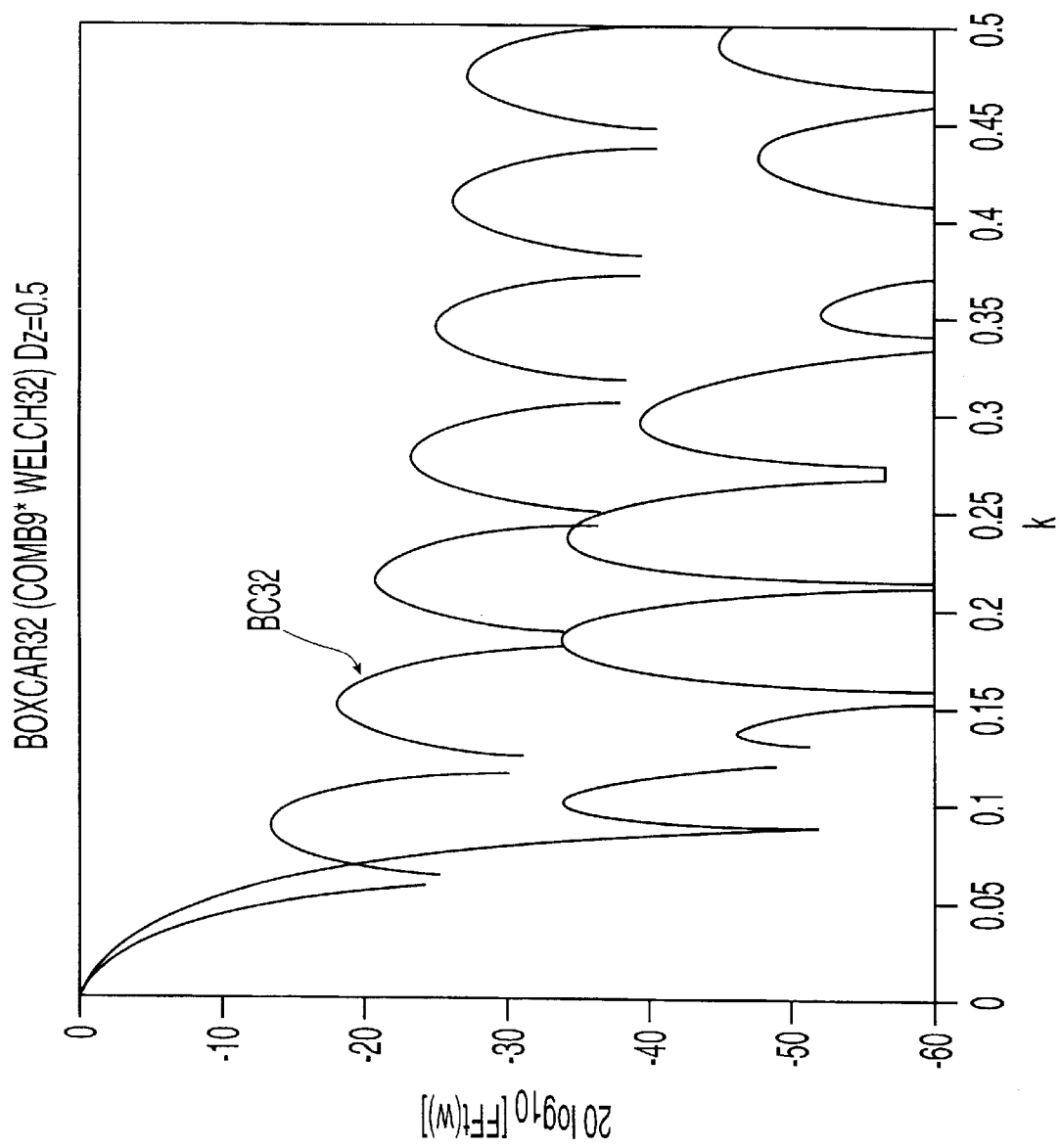
Figure 18:
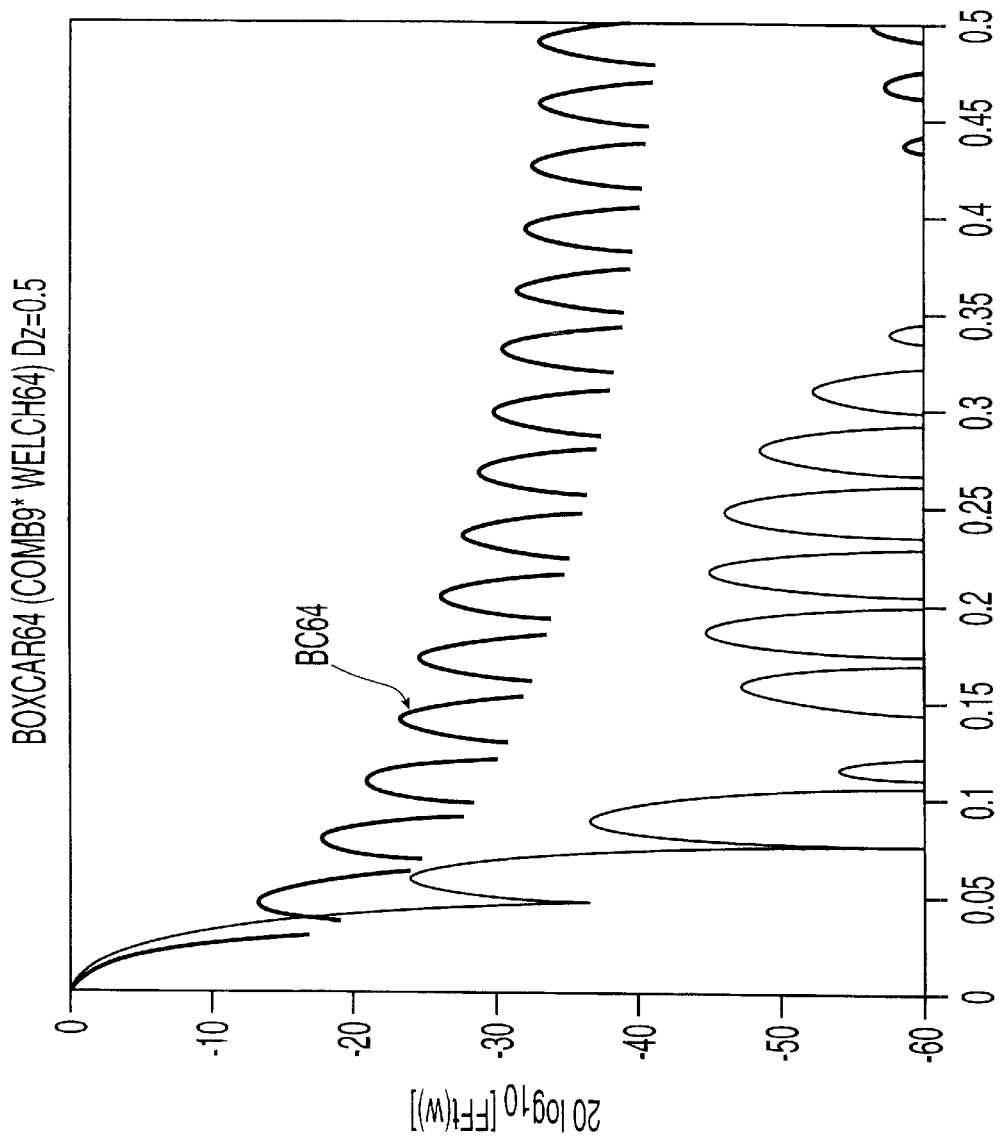

Filter responses for BC32 and BC64, vs. C9HM32 and C9HM64, respectively, can be seen in FIGS. 17 and 18. As the RA gets larger, the locations of the first notch in both filters converge. However, the secondary peak in the C9HM32 or C9HM64 filters is much weaker, resulting in cleaner log response. As illustrated in FIG. 17 for a comparison of BC32 and C9HM32 filters, the notch in the CM9HM32 filter occurs at a higher spatial-frequency, thereby increasing the inherent vertical resolution. Also note the weaker side-lobe (compared to C9HM32), after the first notch.

FIG. 18 illustrates a comparison of the BC64 and C9HM64 filters. The inherent vertical resolution of the C9HM64 filter clearly is better, since the first notch occurs at a higher spatial-frequency compared to the BC64 filter.

LOG EXAMPLES

Non-dithered MRIL-C Log

Figure 19:
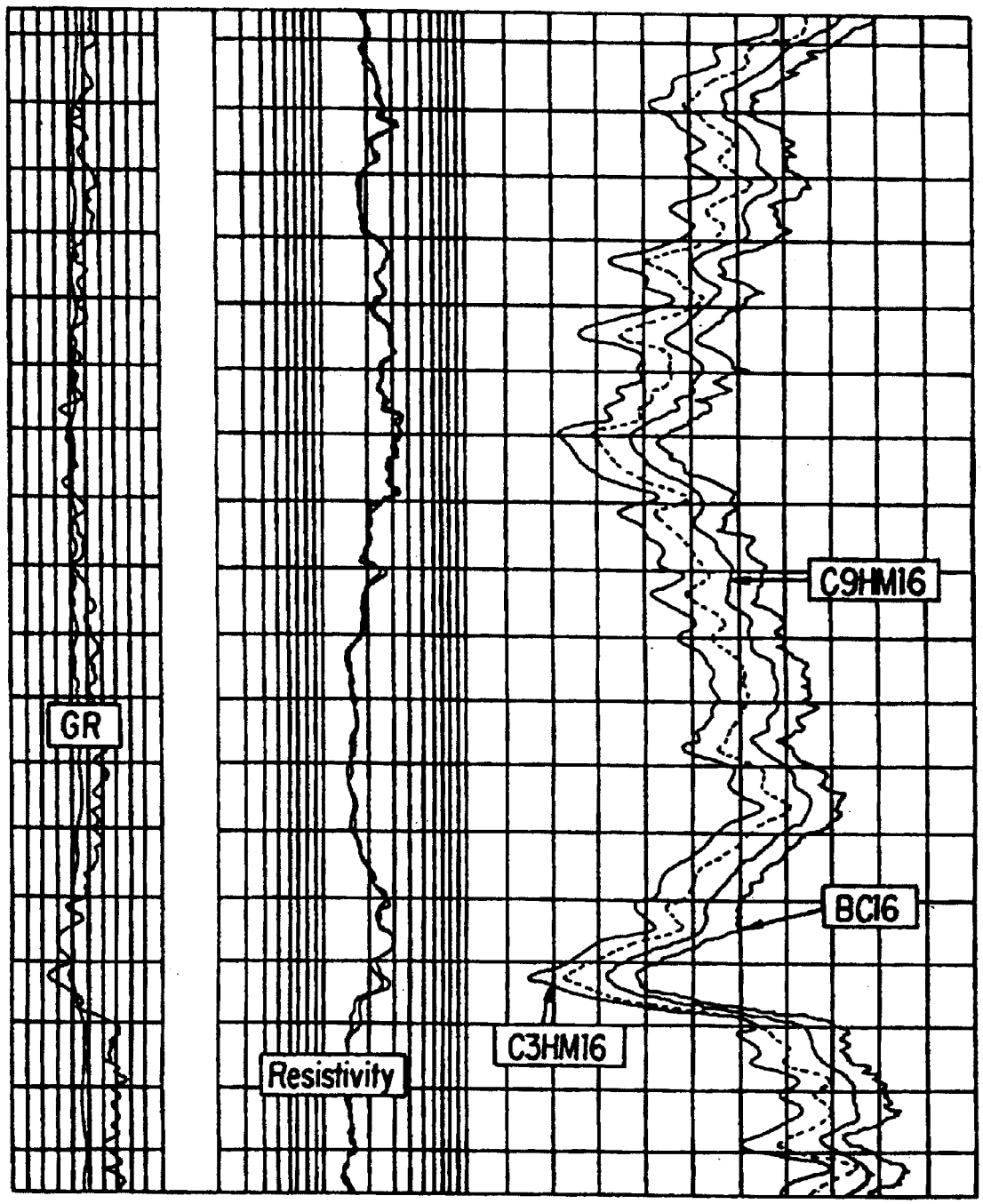
FIG. 19 illustrates the application of four filters, to a 1995-vintage, dual-frequency MRIL-C log.

The four filters, BC16, C3HM16, C5HM16, and C9HM16 were applied to a 1995-vintage, dual-frequency MRIL-C log. The activation used at the time was not dithered. The results of the four filters can be seen in FIG. 19. The logs have been offset by a constant amount to allow easier visual identification of the features. Porosity from the conventional BC16 process is the red curve, easily identified by jittery noise. The black curve corresponds to the C3HM16 filter, which has the best vertical resolution and the most stable appearance. The other two curves, corresponding to C5HM16 and C9HM16 filters, are also better than the BC16 case, but not as good as the C3HM16 filter. Note the excellent agreement between the theory and the results.

MRIL-C Log, BA Test Well, 6 Second Wait Time

Figure 20:
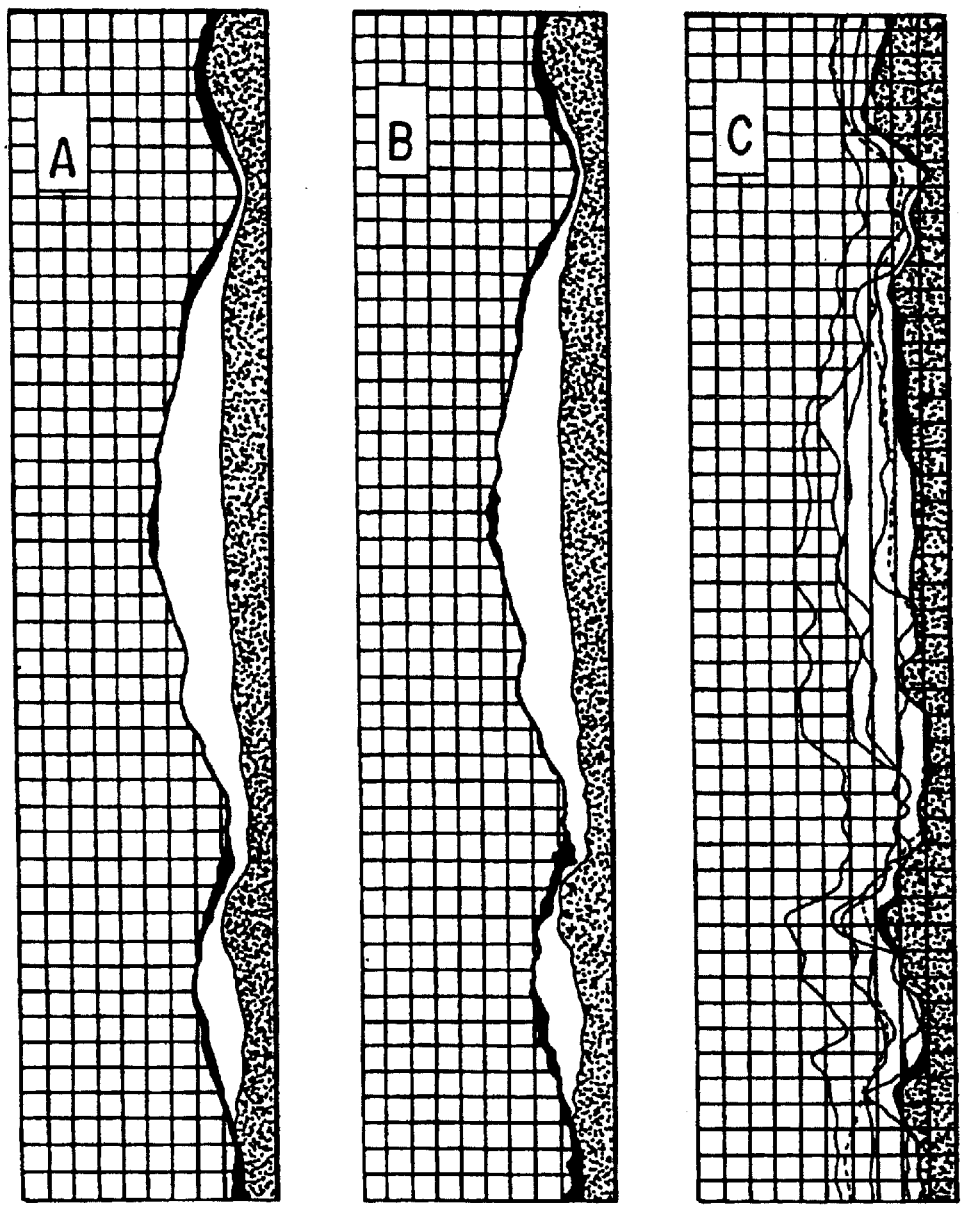
FIGS. 20 and 21 show a comparison of standard processing, versus the method of this invention, in a Baker-Atlas well, MRIL-C log, 6 and 3 second wait time, respectively.
Figure 21:
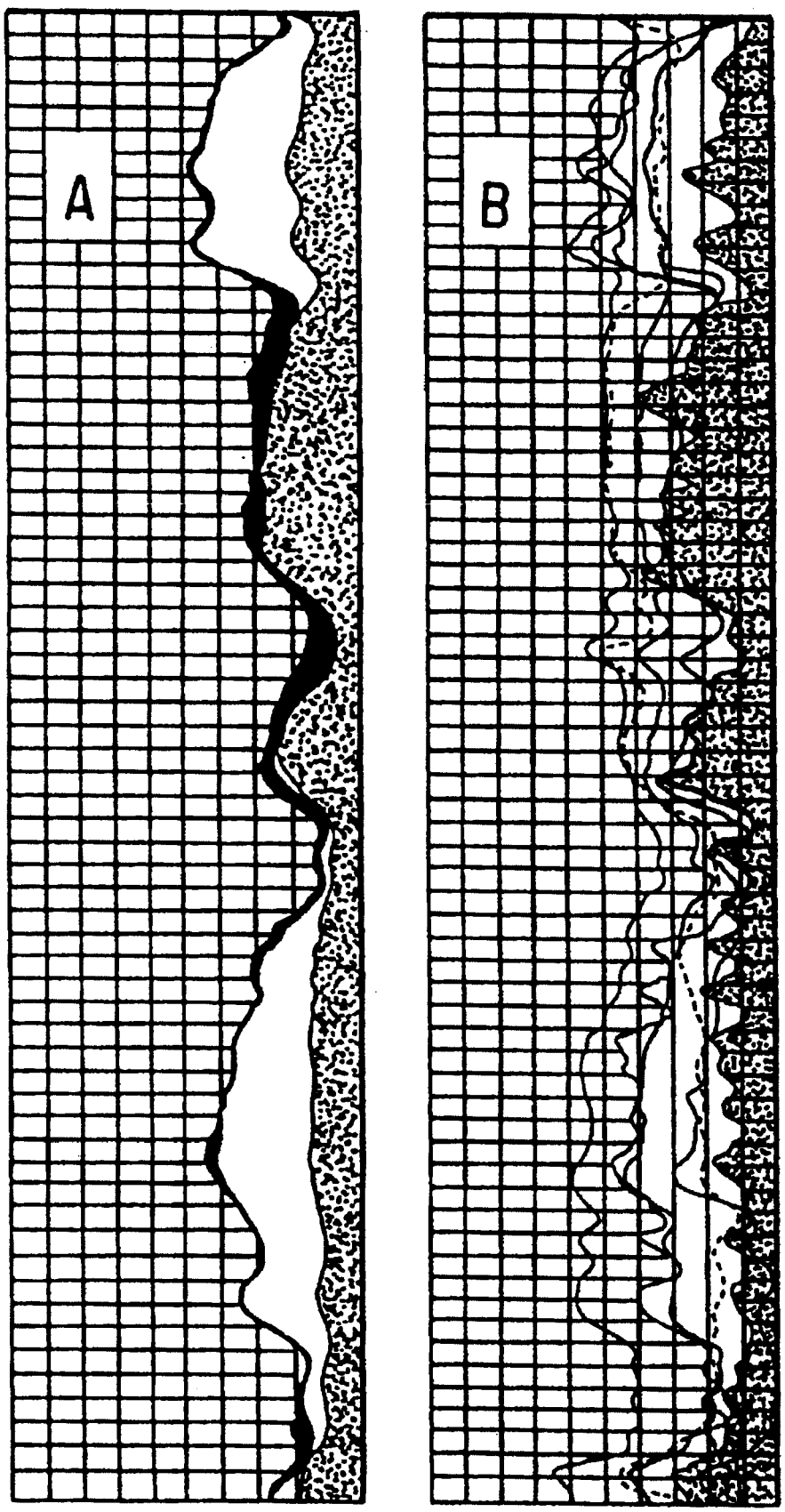

A comparison of standard processing, vs. the method of this invention, in a Baker-Atlas well are shown in FIGS. 20 and 21. Log A is standard MRIL boxcar processing, with a post-inversion cosine filter applied, while B is the same log without the cosine filter. Log C shows results from the new method, with clear improvements in vertical resolution. FIG. 20 is a Baker-Atlas Test Well, MRIL-C log, 6 second wait time. FIG. 20(A) illustrates standard MRIL boxcar processing with post-inversion cosine filter; FIG. 20(B) is the same as (A), without the cosine filter; and FIG. 20(C) illustrates the new method. While porosities in FIGS. 20(A) and (B) contain contributions from the PR06 data set, the porosity log in (C) has been obtained only from the $t_e=1.2$ ms data set.

MRIL-C Log, BA Test Well, 3 Second Wait Time

A comparison of the logs, in the same well, but with a wait time of 3 seconds is shown in FIG. 21. FIG. 21(A) is the standard processing, FIG. 21(B) illustrates the new method. As in the previous figure, the porosity curve in (B) has been obtained from the 1.2 ms data set only. The logging speeds in FIGS. 20 and 21 are close, such that the reduction in the wait time, when using similar stacking levels, results in improved vertical resolution, independent of the method. The zone shown in FIG. 21 covers the same sand in the previous figure, and another shorter zone above it.

Based on the above examples, the following observations can be made: an alternative pre-processing method has been developed to improve the vertical resolution of NMR logs. The methods proposed in Section D replace the boxcar filter with the combination of a comb filter, and a tapered filter, and is equally applicable to a variety of multi-frequency tools.

Next, overall the filter response of the method of this invention is less noisy than the boxcar filter. The side-lobes in the filters (after the first notch) are alternately anti-phase and in-phase with the main-lobe. Consequently, the first side-lobe contributes a strong signal out of phase with the true signal. Hence, a strong first side-lobe will generate appreciable noise (as in the case of boxcar filters), while weaker side-lobes (as in the case of the proposed method) will result in much cleaner response. Indeed, it appears likely that noise originating from the first side-lobe of the boxcar filter is what necessitates the additional application of a cosine filter in the post-inversion phase of the current processing.

In low SNR conditions, where RA»MRA, the proposed method can significantly enhance the vertical resolution of both the MRIL-C and MRIL-D tools, while significantly reducing filter side-lobe noise.

In high SNR conditions (such as oil-based mud, high frequency operation, etc.), the proposed method can significantly enhance the vertical resolution of MRIL-C logs. The improvements are more dramatic in the case of non-dithered activations.

Although a Hamming filter has been used in a specific embodiment illustrated in the drawings, a large selection of filters exists in literature, which can be used in alternate embodiments, dependent on the particular application and ease of implementation.

D.3 Implementation issues

Figure 22:
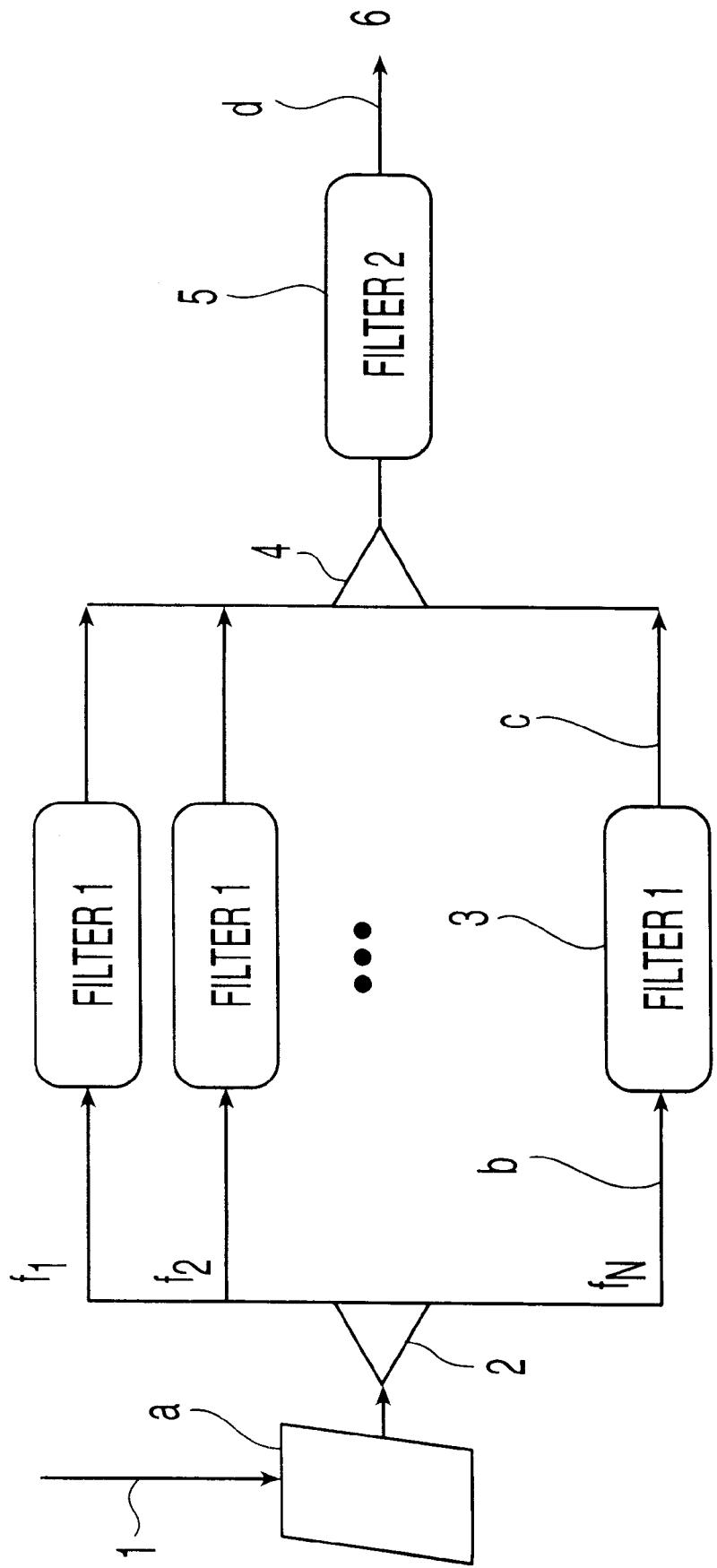
FIGS. 22, 23 and 24 illustrate in more detail the method of the present invention replacing standard box-car processing with a two-stage filtering.

FIGS. 22, 23 and 24 illustrate in more detail the implementation of the method of the present invention discussed in Section D of the disclosure. More specifically, FIG. 22 illustrates in a flow-diagram form the use of two filters to replace the single boxcar filter employed by the prior art.

As illustrated in FIG. 22, the first step 1 (single digit reference numerals in FIGS. 22–24 designate steps) is of acquisition & storage of a depth-varying sequence of multi-frequency PAP echo trains, which are designated in the figure for purposes of illustration as echo trains "a". In the following step (step 2) of the method the multi-frequency echo-trains input signal is separated into multiple data-flow paths, one path per frequency, resulting in N data flow paths, corresponding to the operating frequencies of the tool.

In the following step 3 of the processing algorithm, Filter 1 is applied separately to the data "b" in each data-flow path, producing as the output from each path a sequence of "clean" echo-trains "c" referenced to the mid-point of each echo-train PAP. In the context of this application "clean" denotes that the echo trains no longer contain the non-formation signals that the PAP method or the methods discussed in Sections A, B and C of this application are designed to remove.

In the following step 4 of the method, the separate data-flow paths are re-combined into a single data-flow of the clean echo trains; in the following step 5, Filter 2, as discussed above, is applied to the sequence of clean echo-trains in this recombined data-flow path.

Subsequent processing (step 6) of the clean echo-trains "d" using standard procedures, such as MAP inversion, is applied as known in the art.

Figure 23A:
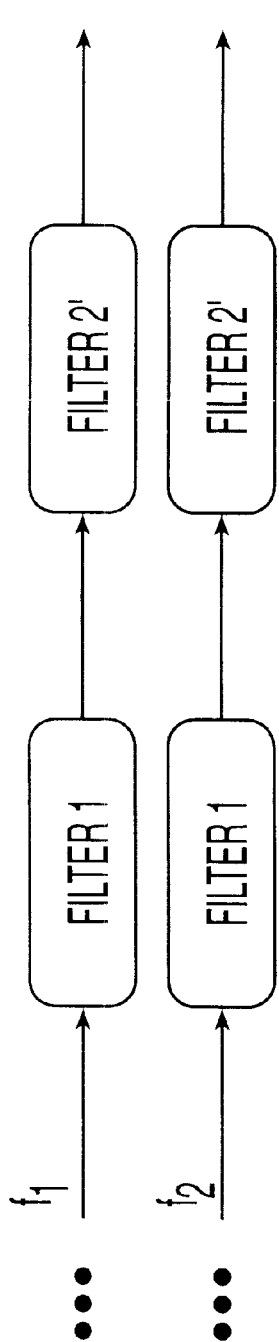
Figure 23B:
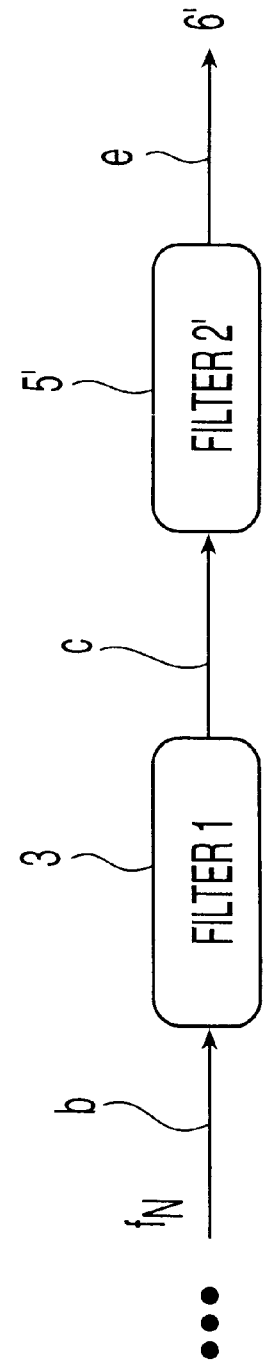

With reference to FIG. 23, an alternative embodiment of the present invention can be used, where the processing modification would allow the user to obtain, for example, the best possible inversions at multiple depths of investigation (lower frequency=>deeper investigation per MRIL design). In particular, and with further reference to the discussion concerning FIG. 22, step 4 of re-combining the data paths is eliminated, so that a separate filter is applied to each data path, as shown in FIG. 23A. In accordance with this embodiment further illustrated in FIG. 23B, a Filter 2' (designed in the same manner as Filter 2 discussed above) is applied (step 5') to obtain optimum vertical resolution for a given SNR—even though the data is much sparser than with the recombined echo-trains—and to produce multiple frequency-separated clean echo trains "e" with optimum vertical resolution for the required SNR. Subsequent processing (step 6') of the frequency-separated clean echo-trains using standard procedures is applied, as known in the art.

Figure 24A:
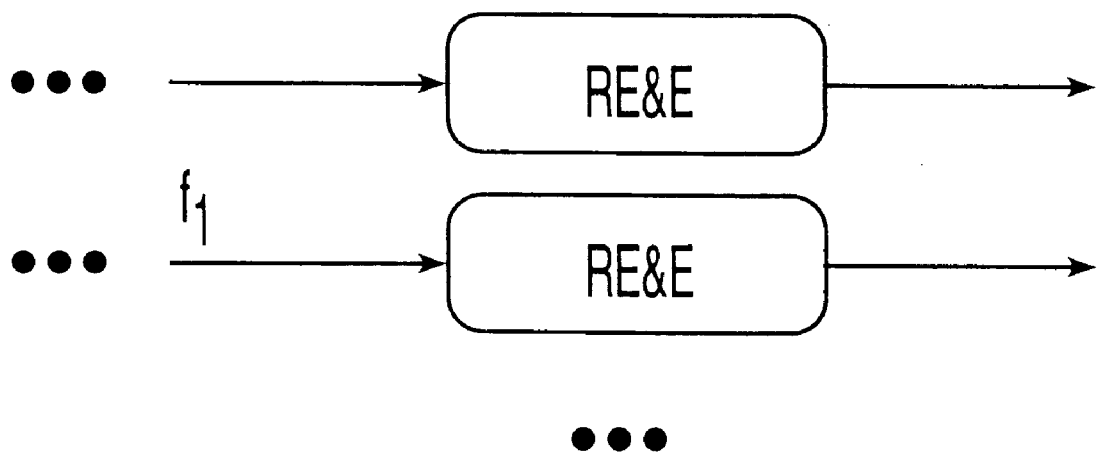
Figure 24B:
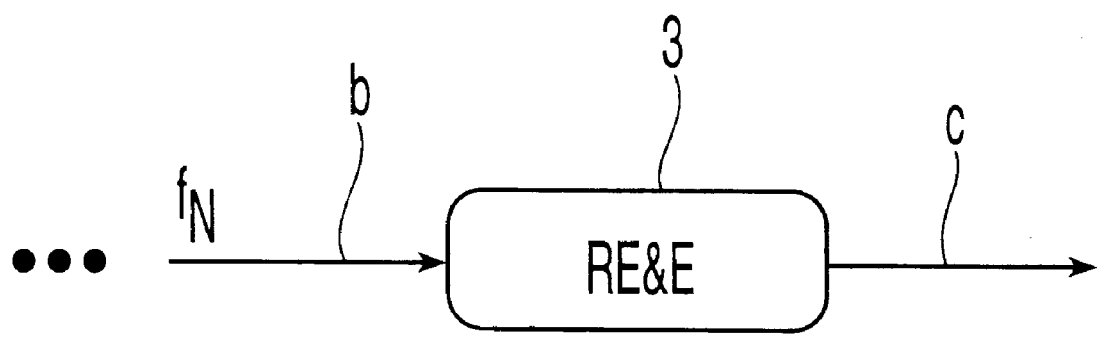

With reference to FIGS. 24A and 24B, in an alternative embodiment, the filtering in Step (3) could be replaced by (3') the data-driven determination of the ringing signal with subsequent removal from the echo-trains. Data driven determination of the ringing signal is discussed in more detail in Section A of this application. [RE&E—Ringing Estimation & Elimination]. Subsequent processing can be either with steps (4), (5) and (6), or with steps (5') and (6'), as described previously, or with other methods not explicitly described.

E. Overall System and Method Considerations

In accordance with the present invention, and as also indicated above, the methods disclosed in Sections A, B, C and D can be used advantageously in combination. It is noted first that the method in Section D, can be used to replace boxcar filtering in all practical applications. In the more special case when the SNR of the formation data is sufficiently high, it can be supplemented with processing of the type discussed in Sections A–C.

More specifically, in a preferred embodiment a NMR system for data logging and analysis is operated as follows. First, the method disclosed in Section D is initially applied and used to estimate the SNR, which is obtained from the input data. Next is determined if the vertical-resolution is sub-optimal and, if so, the processing is switched to the ringing estimation method discussed in Sections A–C.

In an alternative embodiment, one can start by using the Direct Ringing Estimation approach discussed in Section A.1.b; based on the results from this step one can then estimate what filter length is needed to obtain adequate SNR. If the estimated filter length is consistent with the approach discussed in Section D, the operation is switched for this processing.

In general, it will be noted that the filtering approach disclosed in Section D is likely to be more robust, as it does not make any assumptions about the ringing signal other than that it is essentially unchanged between any two echo-trains that make up a PAP. The estimation of ringing, on the other hand, makes some assumptions about the ringing signal, which in the preferred embodiment is quite simple, i.e., that the ringing signal is characterized by an offset (in the complex space) to the real and imaginary components in the NMR signal, which remain essentially unchanged between any two echo-trains that make up a PAP.

The combination discussed above is believed to be a significant contribution to the art of NMR logging with wide ranging applications involving virtually all NMR tools, and a broad range of practical applications, including logging while drilling.

While the invention has been described with reference to the preferred embodiments, it will be appreciated by those of ordinary skill in the art that modifications can be made to the structure and form of the invention without departing from its spirit and scope which is defined in the following claims.

What is claimed is:

1. A method for determining properties of geologic formations using nuclear magnetic resonance (NMR) techniques, comprising the steps of:

providing a plurality of phase alternated NMR pulse echo trains from a geologic formation;

estimating non-formation signal contribution in the plurality of NMR pulse echo trains;

removing the estimated non-formation signal contribution from at least some of the plurality of NMR pulse echo trains; and determining properties of the geologic formation based at least in part on NMR pulse echo trains in which the estimated non-formation signal contribution had been removed.

2. The method of claim 1 in which the NMR pulse echo trains are Carr-Purcell-Meiboom-Gill (CMPG) spin echo trains.

3. The method of claim 2 wherein non-formation signal contribution is estimated from two or more of the plurality of CPMG spin echo trains.

4. The method of claim 3 wherein non-formation signal contribution is estimated using one or more phase-alternated pair(s) (PAPs) of CPMG spin echo trains.

5. The method of claim 4 wherein two PAPs are used, which PAPs are formed by a current CPMG spin echo train ($CPMG_0$) and an immediately preceding ($CPMG_{-1}$) and an immediately following ($CPMG_{+1}$) phase alternated CPMG spin echo trains.

6. The method of claim 5 wherein non-formation contribution signal is defined as ringing and, two ringing estimates are defined, using $CPMG_0$, $CPMG_{-1}$ and $CPMG_{+1}$, as follows:

$$\text{Ringing}_{-1}(n) = \frac{CPMG_0(n) + CPMG_{-1}(n)}{2}$$

$$\text{Ringing}_{+1}(n) = \frac{CPMG_0(n) + CPMG_{+1}(n)}{2}.$$

7. The method of claim 6 further comprising the step of computing mean ringing averages, according to the expression:

$$\text{MeanRinging}_{-1} = \frac{1}{N}\sum_{n=1}^{N}\text{Ringing}_{-1}(n)$$

$$\text{MeanRinging}_{+1} = \frac{1}{N}\sum_{n=1}^{N}\text{Ringing}_{+1}(n).$$

8. The method of claim 7 further comprising the steps of:

computing a single number MeanRingingAverage, which represents an estimate of the non-formation signal contribution; and computing a corrected signal $CPMG_0'$ using the expression:

$$CPMG_0'(n) = CPMG_0(n) - MeanRingingAverage.$$

9. The method of claim 2 further comprising the step of stacking CPMG spin echo trains from which non-formation signal contributions has been removed to achieve a predetermined signal to noise ratio (SNR).

10. The method of claim 9, wherein 2, 4 or 6 CPMG spin echo trains are stacked to achieve a predetermined SNR.

11. The method of claim 1 wherein non-formation signal contribution is estimated using a separate NMR pulse acquisition sequence.

12. The method of claim 11 wherein the separate NMR pulse acquisition sequence is a CPMG sequence, without an initial $\pi/2$ pulse.

13. The method of claim 12 wherein the separate NMR acquisition sequence is used to obtain a single number MeanRingingAverage, which represents an estimate of the non-formation signal contribution; and computing a clean signal $CPMG_0'$ using:

$$CPMG_0'(n) = CPMG_0(n) - MeanRingingAverage.$$

14. The method of claim 2 wherein $$T_E * f = N$$

so that the product of the echo spacing ($T_E$) in milli seconds and the operating frequency (f) for the CPMG spin echo train(s) is an integer number N.

15. The method of claim 6 wherein the ringing estimates are used to obtain a time-varying ringing function, which is subtracted on a component-by-component basis from at least one NMR pulse echo train to obtain a corrected NMR pulse echo train.

* * * * *